(12) United States Patent
Hasan et al.

(10) Patent No.: US 9,974,535 B2
(45) Date of Patent: May 22, 2018

(54) METHOD OF SUTURING TISSUE

(71) Applicant: Surgimatix, Inc., Elk Grove Village, IL (US)

(72) Inventors: Jafar Syed Hasan, Oak Brook, IL (US); Wai Ngai Chin, Glenview, IL (US); Gary Michael Kobylewski, Hoffman Estates, IL (US)

(73) Assignee: Surgimatix, Inc., Hillside, IL (US)

( * ) Notice: Subject to any disclaimer, the term of this patent is extended or adjusted under 35 U.S.C. 154(b) by 568 days.

(21) Appl. No.: 14/630,356

(22) Filed: Feb. 24, 2015

(65) Prior Publication Data

US 2015/0164501 A1 Jun. 18, 2015

Related U.S. Application Data

(62) Division of application No. 13/332,720, filed on Dec. 21, 2011, now Pat. No. 9,844,367.

(Continued)

(51) Int. Cl.
*A61B 17/04* (2006.01)
*A61B 17/06* (2006.01)
*A61B 17/29* (2006.01)

(52) U.S. Cl.
CPC ...... *A61B 17/0469* (2013.01); *A61B 17/0483* (2013.01); *A61B 17/0491* (2013.01);
(Continued)

(58) Field of Classification Search
CPC ........ A61B 17/0469; A61B 2017/0472; A61B 2017/0498
See application file for complete search history.

(56) References Cited

U.S. PATENT DOCUMENTS 5,417,700 A 5/1995 Egan
5,470,338 A * 11/1995 Whitfield ........... A61B 17/0469
112/169

(Continued)

OTHER PUBLICATIONS

Chinese Office Action Application No. 201180062595.8 dated Nov. 16, 2015.
Australian Examination Report for related Australian Application No. 2011849176; dated Mar. 18, 2016.
(Continued)

*Primary Examiner* — Sarah W Aleman
(74) *Attorney, Agent, or Firm* — Miller, Matthias & Hull LLP

(57) ABSTRACT

A medical device for installing sutures to close an incision in tissue or human skin is disclosed. The suturing device may provide first and second arcuate needles. Once properly positioned, the first and second arcuate needles are driven through the sub-dermal layer, or alternatively through a superficial surface, of two sections of skin to be joined. This is done in arcuate fashion and at identical and symmetrical rates of angular displacement. In so doing, the sections of skin are pushed toward one another thus assuring horizontal and vertical alignment of the two sections of skin. During the driving or retraction process of the first and second arcuate needles, a suture is positioned within both the first and second sections of skin and transformed from a planar or a multi-planar serpentine orientation to a helical orientation. The resulting suturing process is thus much faster than conventional or manual suturing and results in superior wound approximation/alignment that will lead to decreased scarring compared to prior art devices.

9 Claims, 38 Drawing Sheets

Related U.S. Application Data

(60) Provisional application No. 61/427,003, filed on Dec. 23, 2010.

(52) U.S. Cl.
CPC ..... *A61B 17/0482* (2013.01); *A61B 17/06066* (2013.01); *A61B 17/06166* (2013.01); *A61B 17/29* (2013.01); *A61B 2017/0472* (2013.01); *A61B 2017/0498* (2013.01); *A61B 2017/0608* (2013.01); *A61B 2017/06042* (2013.01); *A61B 2017/06176* (2013.01); *A61B 2017/2941* (2013.01)

(56) References Cited

U.S. PATENT DOCUMENTS

| | | |
|---|---|---|
| 7,056,331 B2 | 6/2006 | Kaplan et al. |
| 8,961,560 B2 | 2/2015 | Avelar et al. |
| 8,968,362 B2 | 3/2015 | Thomas et al. |
| 2002/0175091 A1 | 11/2002 | Williamson, IV et al. |
| 2006/0069397 A1 | 3/2006 | Nobles et al. |
| 2009/0093824 A1 | 4/2009 | Hasan et al. |
| 2009/0248070 A1 | 10/2009 | Kosa et al. |
| 2010/0113873 A1 | 5/2010 | Suzuki et al. |
| 2011/0251639 A1 | 10/2011 | Thomas et al. |

OTHER PUBLICATIONS

European Search Report for related European Application No. 11849954.0 dated Jan. 11, 2016.

\* cited by examiner

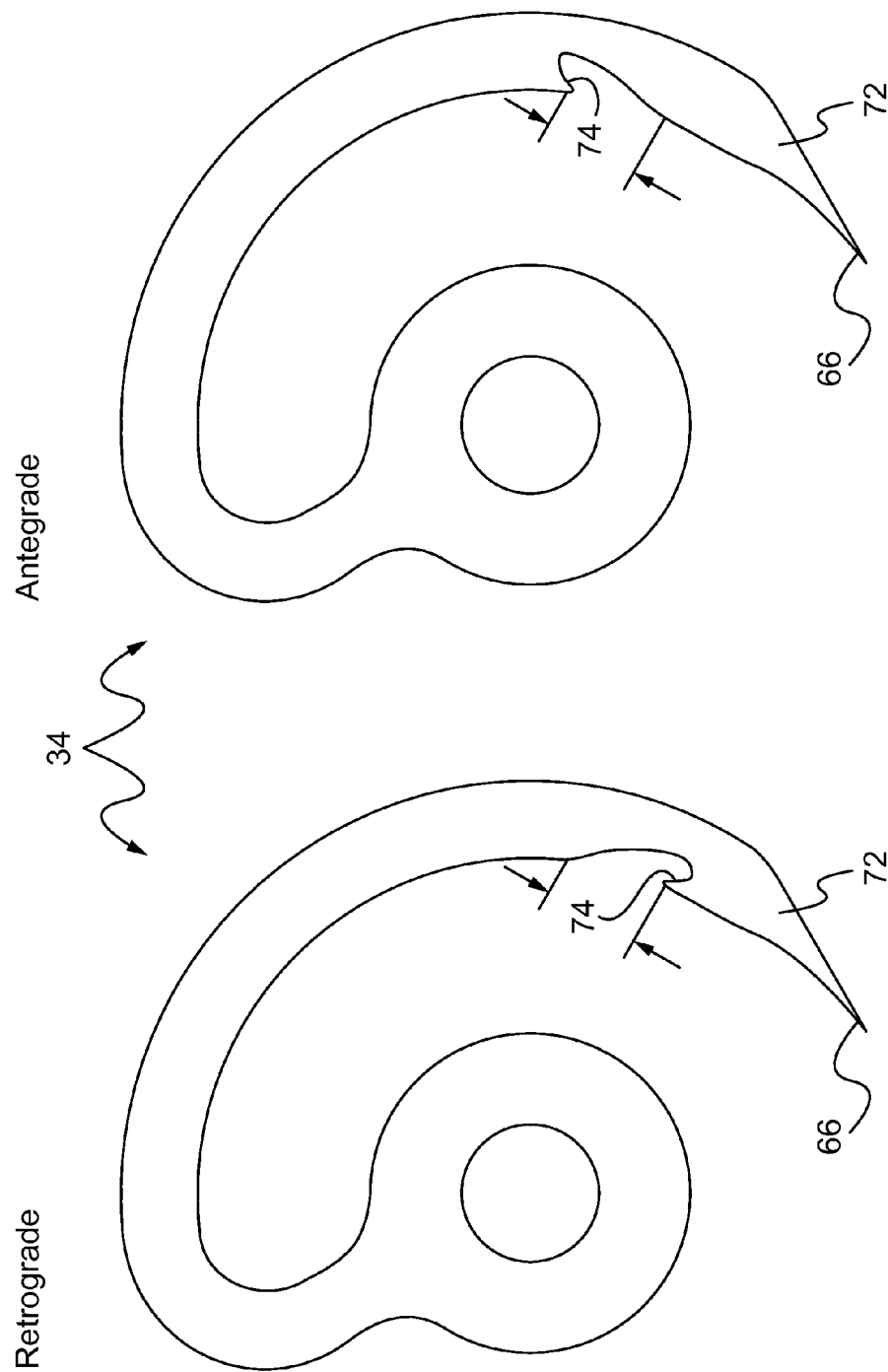

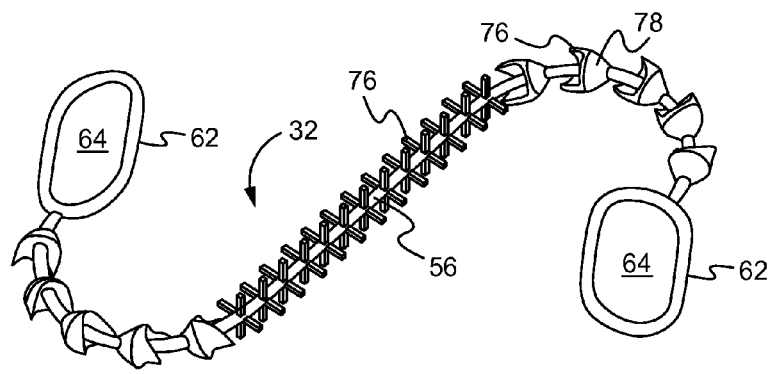
Fig. 11E
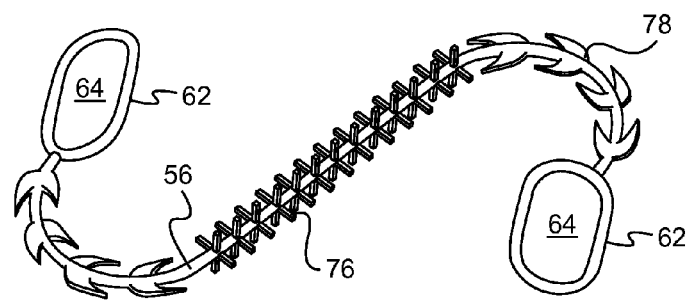
Fig. 11F
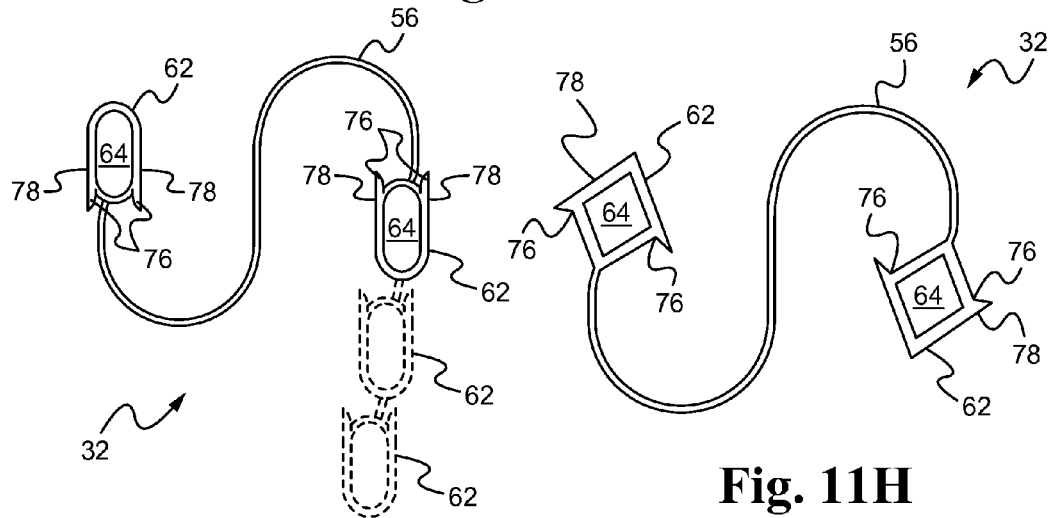
Fig. 11G
Fig. 11H

Prevents retraction and medialization of ends of fastener in tensioned closed helical state, and centers the fastener

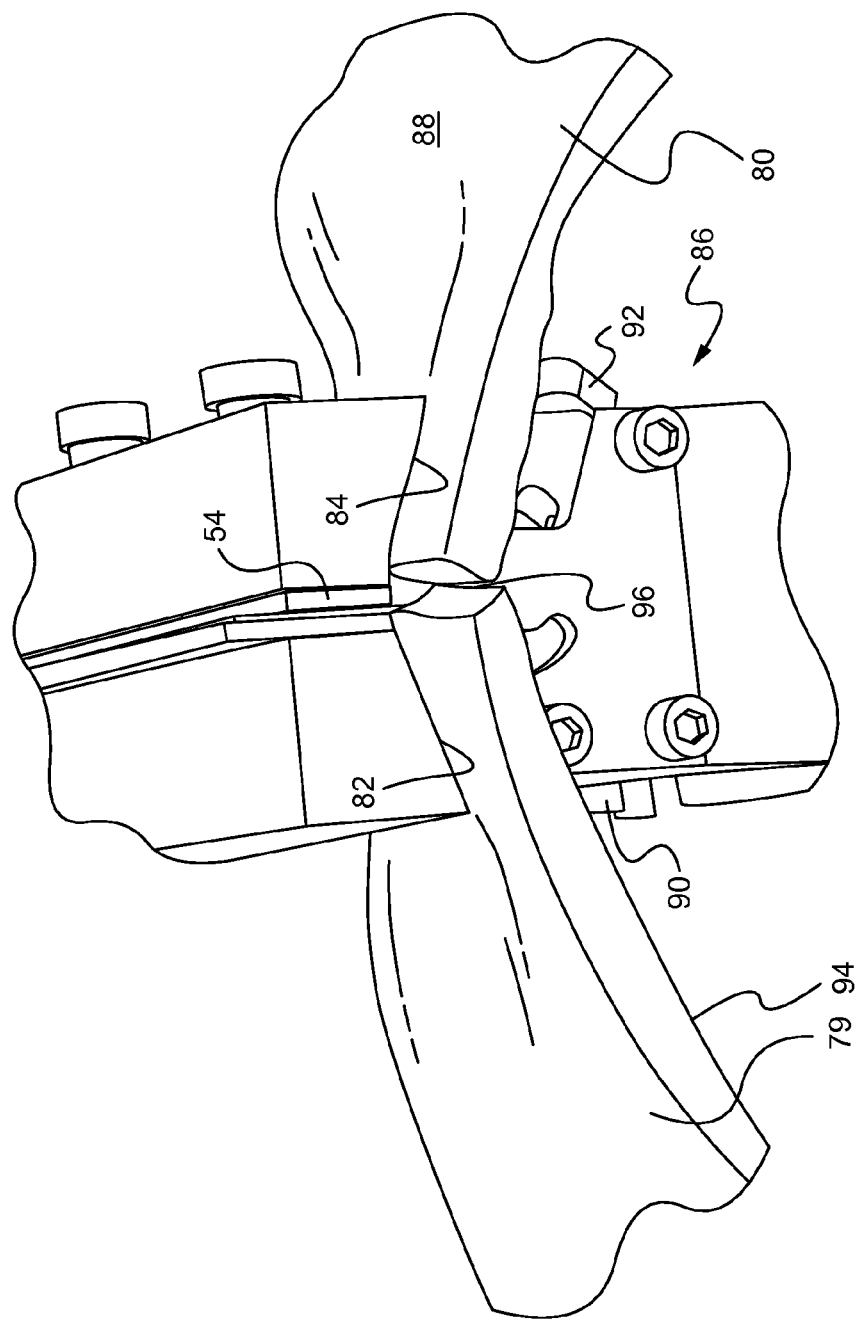

METHOD OF SUTURING TISSUE

CROSS-REFERENCE TO RELATED APPLICATION

This application is a divisional of U.S. non-provisional patent application Ser. No. 13/332,720, filed on Dec. 21, 2011, which in turn claims the benefit of U.S. Provisional Application Ser. No. 61/427,003, filed on Dec. 23, 2010.

FIELD OF THE DISCLOSURE

The present disclosure generally relates to medical devices, and more particularly relates to medical devices for suturing skin.

BACKGROUND OF THE DISCLOSURE

The closure of incisions or lacerations in human skin has long been a need in the medical industry. Whether the incision is the result of surgeries such as cosmetic surgery or internal organ operations, or those generated by traumatic events or accidents, surgeons are continually presented with patients needing closure of such skin openings. For example, modern studies indicate that approximately 30 million such operations are performed each year in the U.S. alone.

In closing such incisions, surgeons are able to choose from a relatively limited number of options currently available. One of those options is manual suturing. This is perhaps the oldest of the available options and conventionally involves the physician directing a needle, to which is temporarily attached a suturing filament, through one section of skin, across the incision and into the other side of the incision. This process is repeated as many times as necessary to result in a certain number of "stitches" closing the incision. Upon reaching the end of the incision, the physician ties off the last suture to complete the process. While effective, manual suturing is certainly not without its drawbacks. For example, in the case of body contouring surgery, relatively large incisions in excess of many centimeters may be made which can often take the surgeon a very long time to close. It is not uncommon for the suturing of the incision to take longer than the actual operation itself. Not only is it time consuming, but surgeons often view the process as tedious. Moreover, the repeated movement of the needle through the skin of the patient necessarily increases the risk to the surgeon or assistant of being exposed to a needle prick which in turn can lead to certain transmissions of diseases including but not limited to Hepatitis C and HIV.

Given the time and difficulty involved with manual suturing, another closure option which is commonly employed is referred to as stapling. This process typically uses metal staples that are reminiscent of the staples commonly used in office settings to clip papers together. Specifically, stapling involves directing first and second parallel prongs of the staple into the first and second sections of skin to be connected, and against an anvil-like surface provided on the outside of the incision. When the prongs penetrate through the skin and contact the anvil, the prongs are deformed so as to be transverse to the main body of the staple and thus secured in position. The prongs are typically canted slightly inwardly so as to facilitate this deformation. The staples are installed using a medical device typically having some form of spring biased drive mechanism to quickly and effectively deploy the staples.

While significantly faster than manual suturing, staples themselves are also associated with certain drawbacks. Foremost among those drawbacks is the significant scarring associated with staples. The scarring is often referred to as "railroad tracks", as the scar will typically include the linear incision itself laterally flanked by pairs of matching demarcations where the prongs of the staple enter the skin. Moreover, staples are significantly more painful to the patient in that they need to be removed after being installed and after the incision is healed. Suturing, on the other hand, can often be performed with absorbable sutures which disintegrate or are absorbed by the body after installation.

In light of the foregoing, a still further option currently available to surgeons is known as an absorbable dermal stapler wherein the staples are manufactured from a material or anchor which can be absorbed by the patient. One example of such an absorbable dermal stapler is marketed under the trademark "Insorb™". This can potentially avoid a significant level of pain associated with metal staple removal, but may result in significant scarring or poor wound healing in general. This is due to: (a) less than optimal alignment associated with such absorbable staplers between the two sections of skin to be fastened; (b) poor wound holding strength which can result in areas of wound separation if there is any tension on the wound edges (tension which is not uncommon during the post-operative period) and; (c) and creation of small areas of wound separation where the thick fasteners extrude through the incision (known clinically as "spitting" of the fasteners). In order to most effectively close an incision with minimal scarring, it is advantageous to position the first and second sections of skin so as to both be within the same plane (vertical alignment), and to approximate the skin edges as close together as possible (horizontal alignment). If these sections of skin are not well approximated with regard to horizontal alignment, the resulting scar will be relatively wide as the body will fill in the gap with additional connective tissue. If the wound edges are not well aligned in the vertical dimension, then the scar will heal with a "step-off" which causes the scar to be more prominent.

Current absorbable dermal stapling technology provides less than optimal horizontal and vertical alignment. In addition to ensuring precise alignment of the superficial skin surface (epidermis), optimal wound closures should provide good approximation and support in the deeper strength-bearing layer of the skin (dermis). When the dermis is effectively secured, the wound forms a wound surface that is well aligned but slightly protrusive at the superficial surface, a desirable wound configuration that is clinically known as "eversion." As the wound heals, the eversion gradually settles, resulting in a flat/optimal scar. The converse of eversion is wound inversion, which is characterized by the closed wound edges dipping inward. Inversion must be avoided in order to prevent the wound from forming a scar with a recessed valley appearance. Current dermal staplers attempt to position the wound in an everted fashion. However, the method in which the fasteners hold the wound edges in eversion results in prominent "dimpling" of the skin where the fasteners secure the skin edges, a closure appearance which can cause concern to surgeons when they try dermal staplers for wound closure.

With all these drawbacks in mind, a most recent effort has been made to provide a medical device which provides the fast and efficient closure afforded by staplers, with the decreased scarring associated with suturing. For example, U.S. Publication No. 2009/0093824 discloses a wound closure device which is adapted to position an anchor specifically known as an "H-Type" fastener between first and second sections of skin to be secured. The device includes channels in which the first and second sections of skin are to be positioned and includes a single arcuately shaped rotating needle adapted to enter one section of skin through the sub-dermal layer and carry the H-shaped anchor therewith. While the '824 application attempts to position the first and second sections of skin relative to one another, the use of such an H-shaped anchor does not adequately pull the two sections close together after insertion and thus would result in longer healing times and more scarring than is acceptable. More specifically, the leading prong of the "H" needs to be pulled entirely through the second section of skin in order to deploy. Once it is so deployed and released, the anchor is pulled back by the opposite prong and the normal tension on the wound edges, thus resulting in slack in the anchor and a loose "seam". Moreover, the '824 application uses a complex system of rotating approximation arms to push the first and second sections of skin toward one another prior to insertion of the anchor. Not only does this make the device more complicated and expensive to manufacture and prone to reliability problems, but once the approximation arms are retracted so too are the sections of skin and again the resulting closure does not ensure optimal alignment, which would lead to prominent or otherwise poor scarring.

SUMMARY OF THE DISCLOSURE

In accordance with one aspect of the disclosure, a suturing device is disclosed. The suturing device may comprise a first arcuate needle adapted to rotate in a first direction through a dermal layer of a first section of skin to be sutured and through the dermal layer of a second section of skin to be sutured, a second arcuate needle adapted to rotate in a second direction opposite to the first rotational direction and through a dermal layer of a second section of skin to be sutured and through the dermal layer of the first section of skin to be sutured, and a drive mechanism forcing rotation of the first and second arcuate needles upon activation by a user and adapted to insert a suture detachably attached to the first and second arcuate needles.

In accordance with another aspect of the disclosure, a method of suturing skin is disclosed. The method may position a suturing device proximate first and second sections of skin to be sutured together, drive first and second arcuate needles in opposing directions of rotation into the first and second sections of skin, and deploy a suture connecting the first and second sections of skin upon movement of the first and second needles. The first and second needles may separately enter dermal layers of the first and second sections of skin.

In accordance with yet another aspect of the disclosure, a tissue suture is disclosed. The tissue suture may comprise an elongated filament having first and second ends, a first needle guide positioned at the first filament end, and a second guide surface positioned at the second filament end. The filament may have a pre-insertion orientation and a post-insertion orientation. The pre-insertion orientation may be within at least one plane, and the post-insertion orientation may be helical.

These and other aspects and features of the disclosure will be better understood upon reading the following detailed description when taken into conjunction with the accompanying drawings.

BRIEF DESCRIPTION OF THE DRAWINGS

FIGS. 9A-9B are enlarged plan views of suturing needles constructed in accordance with the teachings of the disclosure;

FIGS. 11A-11J are perspective views of multiple embodiments of sutures constructed in accordance with the teachings of the disclosure;

FIG. 13 is a perspective view of a test fixture version of the suturing device in actual use and shown in an engaged position;

Figure 1:
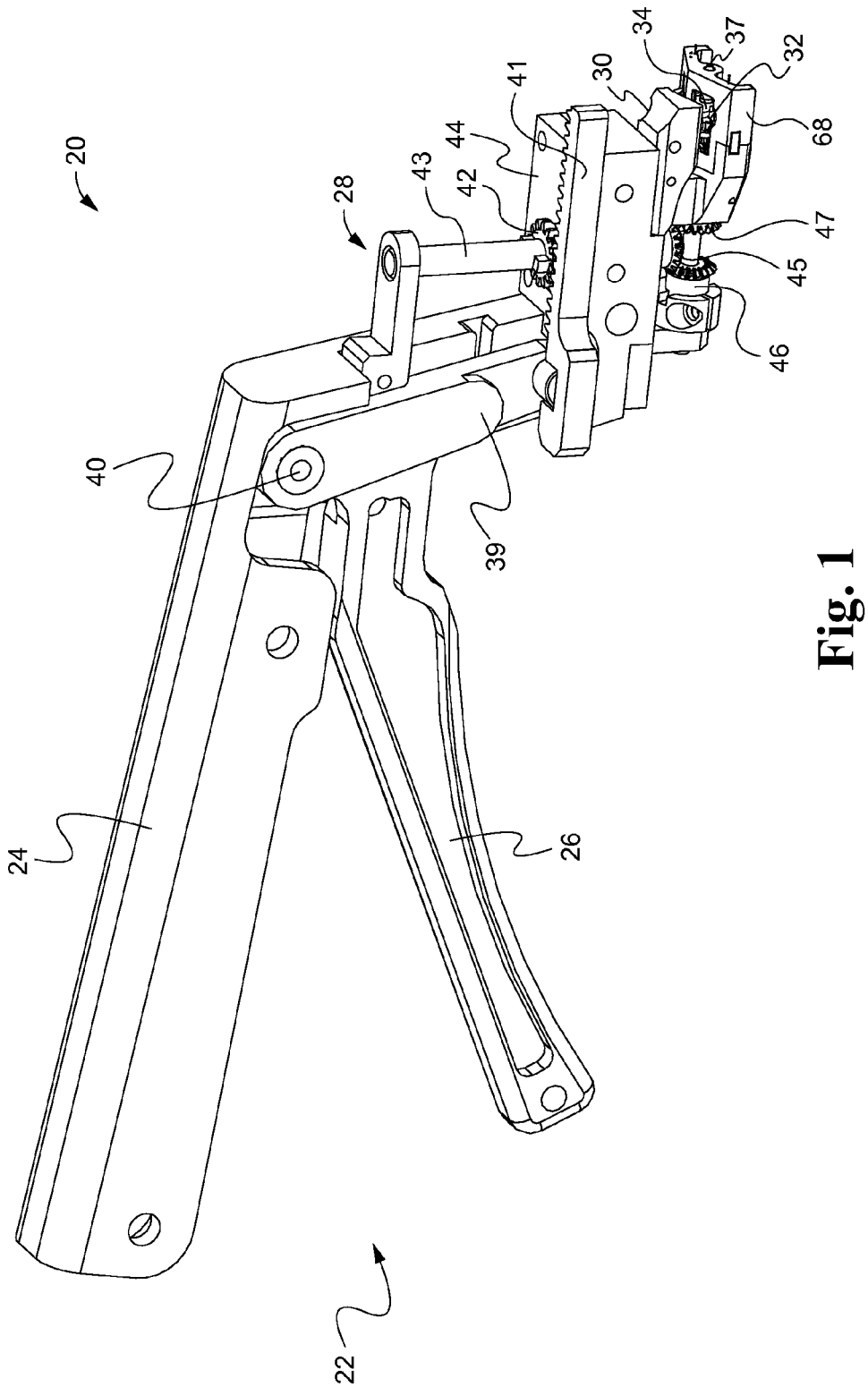
FIG. 1 is a perspective view of a suturing tool constructed in accordance with the teachings of the disclosure.
Figure 2:
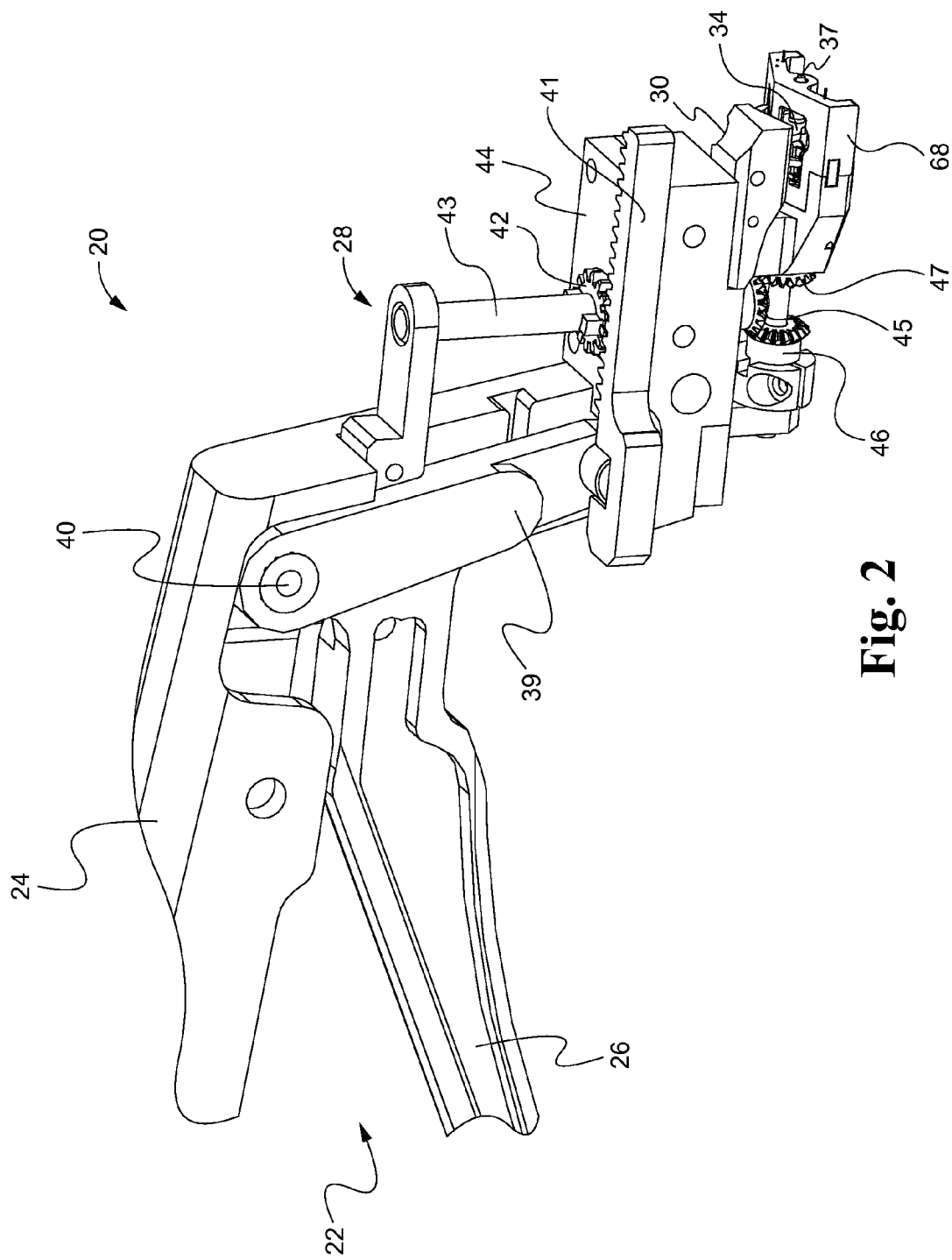
FIG. 2 is an enlarged perspective view of the suturing tool of FIG. 1.
Figure 3:
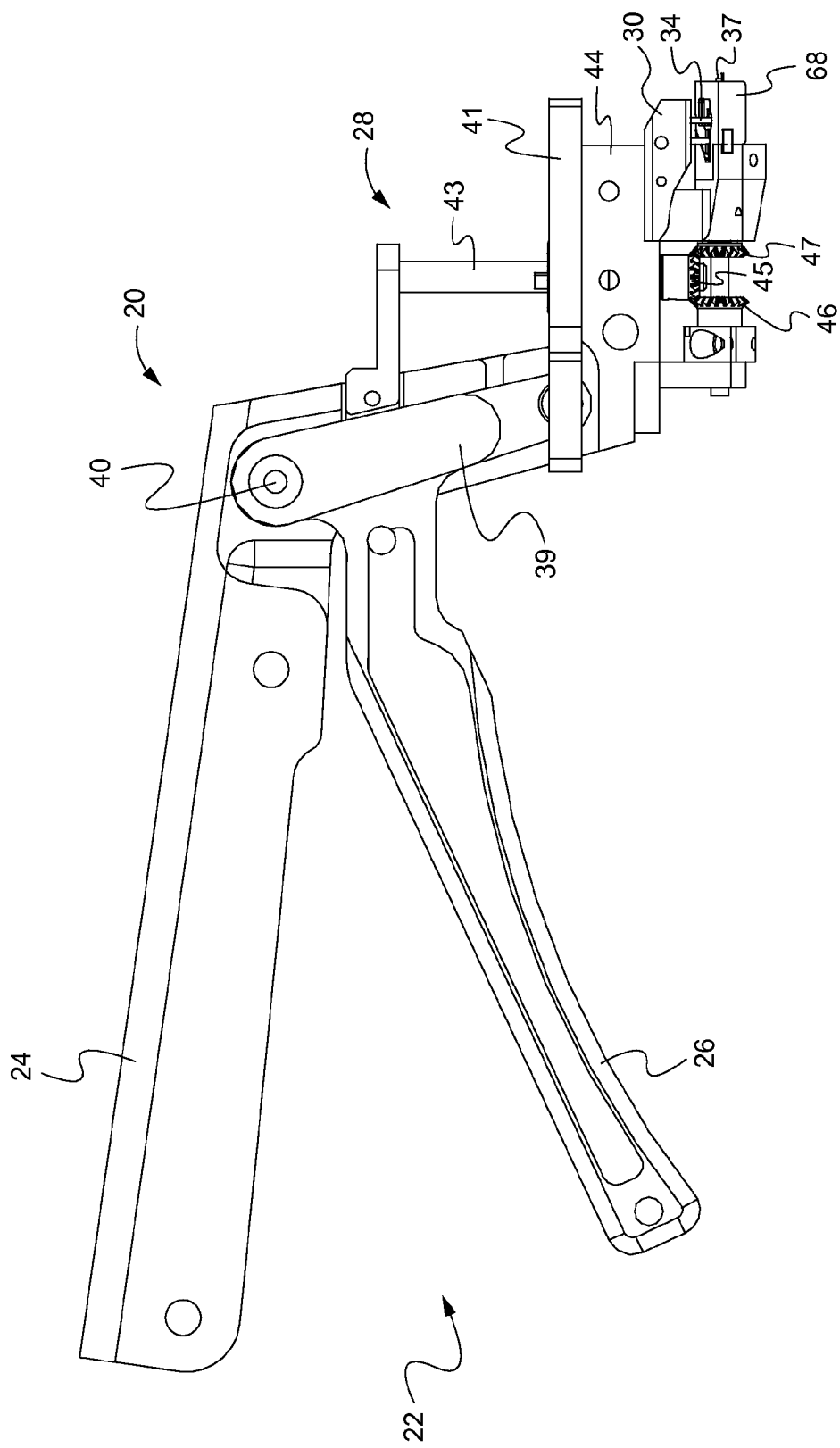
FIG. 3. is a side view of the suturing tool of FIG. 1.
Figure 4:
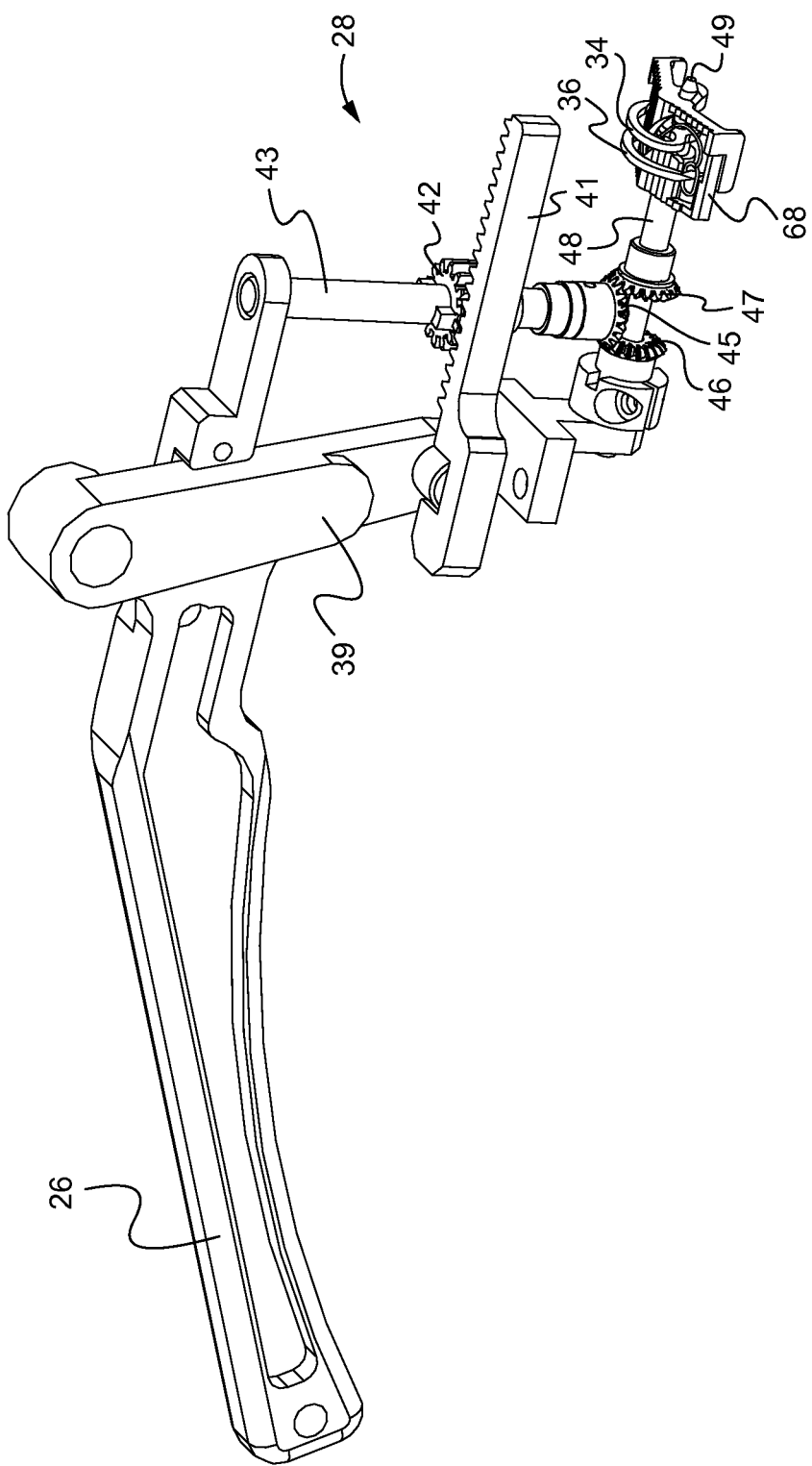
FIG. 4 is a perspective view of the suturing tool of FIG. 1, with certain portions of its exterior cut-away to reveal the drive mechanism of the tool.
Figure 5:
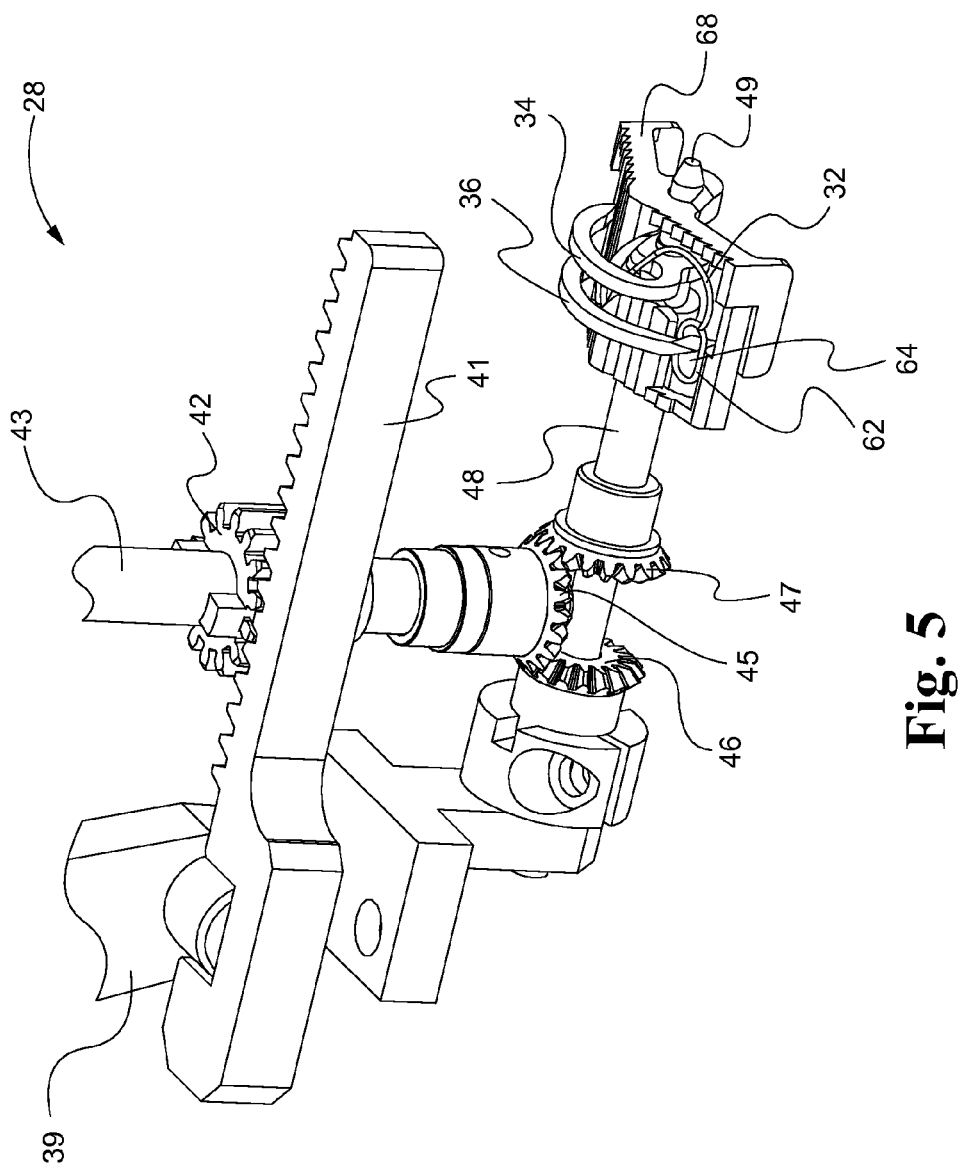
FIG. 5 is an enlarged perspective view of the drive mechanism of FIG. 5.
Figure 6:
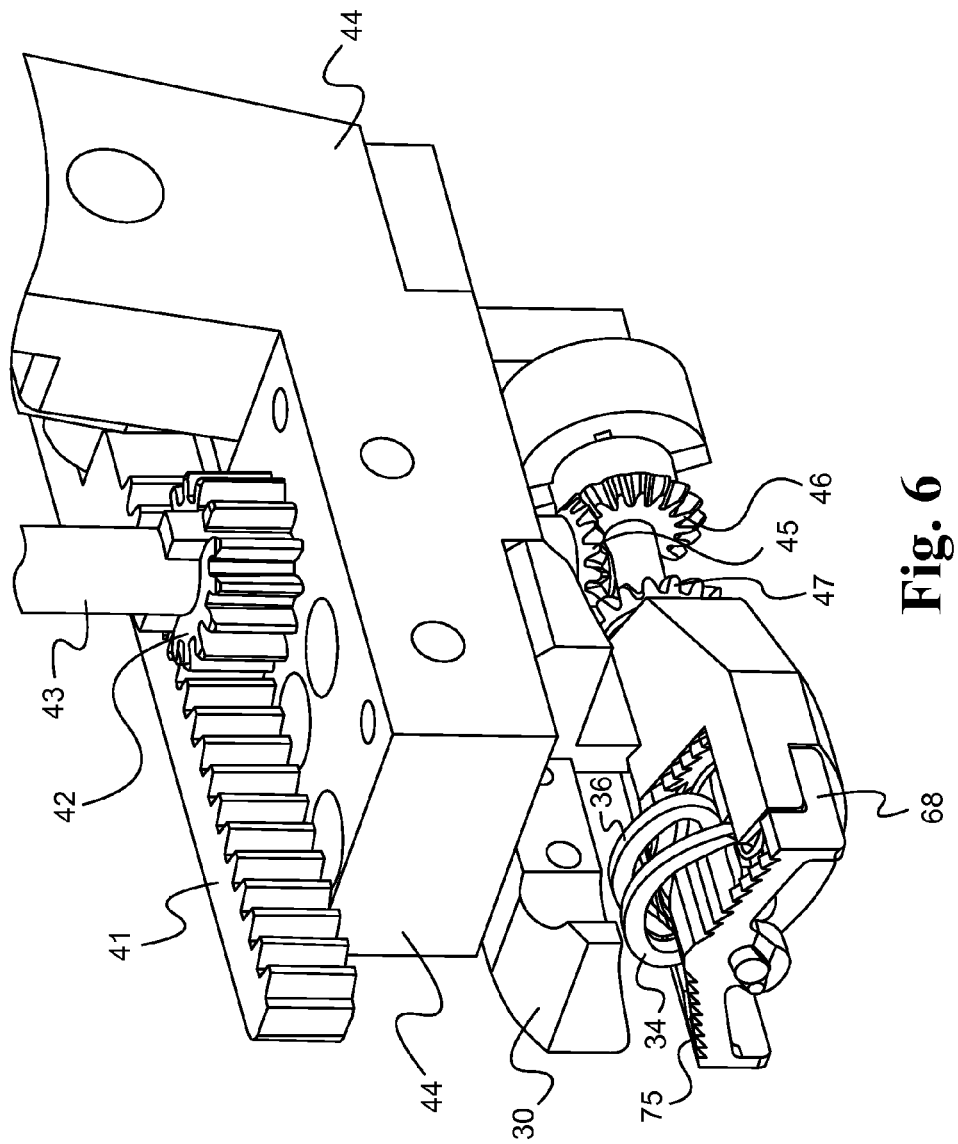
FIG. 6 is an enlarged perspective view of the drive mechanism of FIG. 5, shown from the opposite side of FIG. 5.
Figure 7:
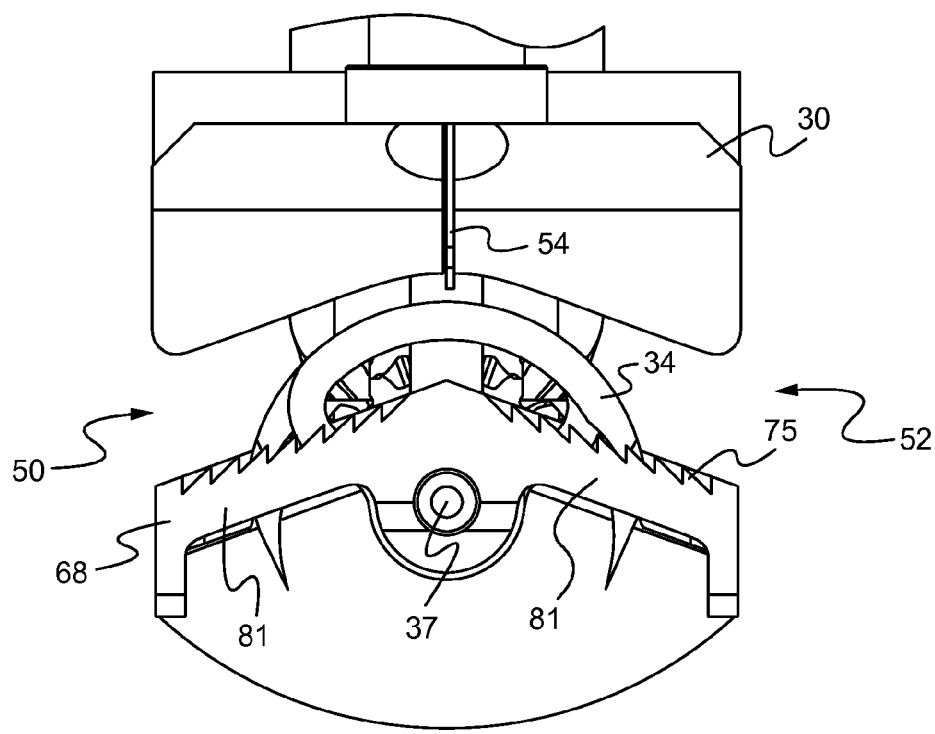
FIG. 7 is an enlarged front view of the operating end of the suturing tool of FIG. 1.

While the present disclosure is susceptible to various modifications and alternative constructions, certain illustrative embodiments thereof have been shown in the drawings and will be described below in detail. It should be understood, however, that there is no intention to limit the present invention to the specific forms disclosed, but on the contrary, the intention is to cover all modifications, alternative constructions and equivalents falling within the spirit and scope of the present disclosure.

DETAILED DESCRIPTION

Referring now to the drawings, and with specific reference to FIG. 1, a suturing device constructed in accordance with the teachings of the present disclosure is generally referred to by reference numeral 20. The device, as will be described in further detail herein, is advantageous for surgically closing incisions, not only quickly, but with closely approximated edges and minimal scarring. Of course, the suturing device 20 can also be used to close lacerations from traumatic events such as accidents, or the like. The first embodiment of FIGS. 1-9 of the suturing tool 20 is designed to be placed under the skin sections of the skin to be sutured, and then place a suture into the dermal layers of the skin. In later described embodiments, suturing tools are described to be used against the epidermal layer of the skin, from the outer skin surface, or be used laparoscopically. Although the embodiments disclosed herein demonstrate suturing as applied to skin, it will be understood that the present disclosure may be equally or similarly applied to tissues other than skin.

Again referring to FIG. 1, it will be noted that the suturing device 20 includes a grip 22 consisting of a handle 24 and a trigger 26. Compression of the trigger 26 toward the handle 24 by the hand of the surgeon causes a drive mechanism 28 to move the internal components of an operating end 30 and thereby install a suture 32 into the dermal layers of skin of a patient (not shown in FIG. 1, but shown later herein).

More specifically, the operating end 30 is shown in further detail in FIGS. 2-7. As will be noted herein, the operating end 30 includes a first arcuate needle 34 and a second arcuate needle 36 adapted to rotate about a common axis 37 as will be described in further detail herein. The motion begins upon compression of the trigger 26 toward the handle 24 which causes a lever arm 39 to rotate about a pivot 40 to thus cause a rack 41 to rearwardly retract. This in turn causes a pinion 42 connected to the drive axle 43, and rotatably journalled in plate 44, to rotate. As shown, the drive axle 43 terminates in a first bevel gear 45 which meshes with second and third bevel gears 46, 47 positioned at right angles relative to the first bevel gear 45. Rotation of the second and third bevel gears 46, 47 causes first and second needles 34, 36 to rotate due to coaxial drive shafts 48, 49 being positioned therebetween. As will be noted, drive shaft 48 is hollow to allow drive shaft 49 to be rotatable therein. Other mechanical and electrical transmissions and gear arrangements, including motorized drive mechanisms, are certainly possible and encompassed within the scope of this disclosure.

FIGS. 4-7 further depict the rotational characteristics of the first and second arcuate needles 34, 36. In an initial or resting position prior to insertion of the suture 32, the first and second arcuate needles 34, 36 are retracted within the operating end 30. Upon compression of the trigger 26 toward the handle 24, the first and second arcuate needles 34, 36 are caused to rotate. By way of example, the needles 34, 36 could rotate approximately 180-270 degrees, but the exact angle may depend on the specific fastener configuration used. In so doing, the first and second arcuate needles 34, 36 are driven through the first and second sections of skin, respectively. Moreover, as will be described in further detail herein, such rotational motion of the first and second arcuate needles 34, 36 can cause the suture 32 to be driven or pulled through the first and second sections of skin, respectively.

FIGS. 4-7 depict the drive mechanism 28 in greater detail. As shown, the operating end 30 includes first and second guide channels 50, 52 adapted to receive first and second sections of skin to be sutured. In addition, the operating end 30 further includes a septum blade 54 therebetween. By providing such an arrangement, where two arcuate needles 34, 36 are rotated toward one another relative to guides 50, 52 and a septum blade 54, the portions of skin being connected are forced toward each other upon activation. This in turn assists in vertically and horizontally aligning the sections of skin and forming a tightly grouped closure.

Figure 8:
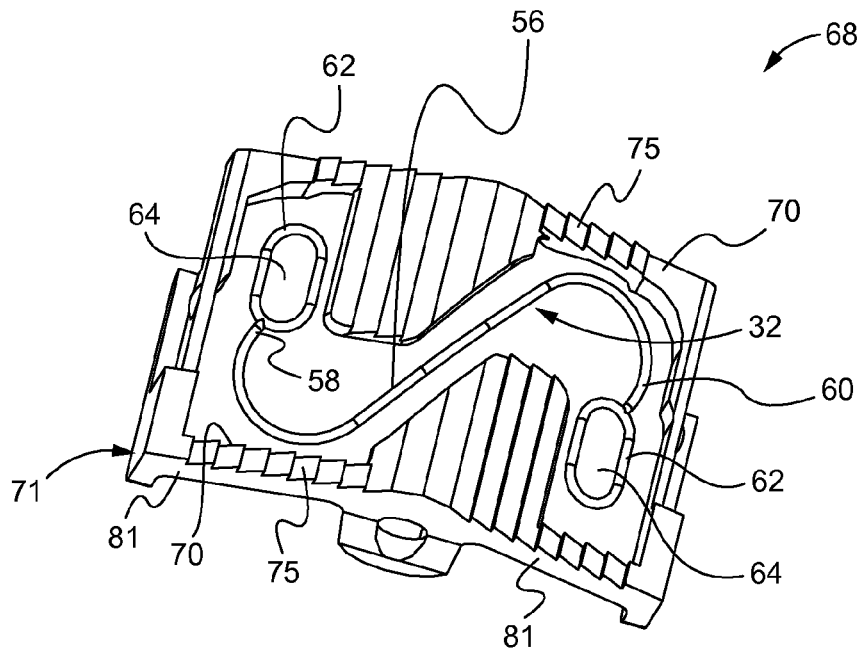
FIG. 8 is a cartridge constructed in accordance with one embodiment of the present disclosure and used in conjunction with the suturing tool of FIG. 1.

While the method of suturing will be described in further detail herein, the structure of the suture 32 will first be described with respect to FIG. 8. As shown herein, in one embodiment the suture 32 may include an elongated filament 56 having first and second ends 58, 60. Each of the first and second ends 58, 60 may terminate with a needle guide 62 to facilitate temporary attachment and release of the suture 32 to one of the first and second arcuate needles 34, 36, respectively. For example, the needle guide 62 may simply be an enlarged diameter aperture 64 which is shaped so as to circumnavigate a terminus 66 of either the first or second arcuate needles 34, 36. The sutures 32 may each be provided within a cartridge 68 as shown in FIGS. 5-8. Moreover, the suture 32 may be temporarily held in the cartridge 68 by frangible connections 70 connecting the suture 32 to a cartridge frame 71 which are broken when needles 34, 36 penetrate or pull termini 66. In alternative modifications, the suture 32 may also be temporarily held in the cartridge 68 by guide channels, grooves, recesses, apertures, or the like.

Additionally, the cartridge frame 71 may include a plurality of serrations 75 to facilitate holding the skin without the need for restraining jaws, or the like. The frame 71 may also include angled side beams 81 for mounting the serrations 75. In so doing, first and second sections of skin (not shown) are held between the angled side beams 81, the guide channels 50, 52, and the septum blade 54 in the aforementioned "everted" position to most effectively form a skin closure with minimal scarring. Furthermore, the cartridge 68 may be configured to be wholly replaceable such that, for instance, a new cartridge 68 may be loaded onto the operating end 30 before each suturing operation. Alternatively, the cartridge 68 may be permanently disposed within the suturing device 20 and configured to receive replaceable sets of sutures 32 before each suturing operation.

As shown in FIGS. 9A-9B, the needles 34, 36 of the suturing device 20, may include tips 72 having recesses 74 to facilitate engagement and removal of the suture 32 from the cartridge 68. In particular, for retrograde applications, where the needle guides 62 are pulled through the skin, the recess 74 of each needle 34, 36 may be outwardly configured to engage the respective needle guide 62 while exiting the skin, for example, upon release of the suturing device 20. Alternatively, for antegrade applications, where the needle guides 62 are driven into the skin, the recess 74 of each needle 34, 36 may be inwardly configured to engage the respective needle guide 62 while entering the skin, for example, upon engagement of the suturing device 20. In still further modifications, the recess 74 may be disposed along the outer surface of the needle 34, 36 rather than the inner surface as shown in FIGS. 9A-9B.

Figure 10A:
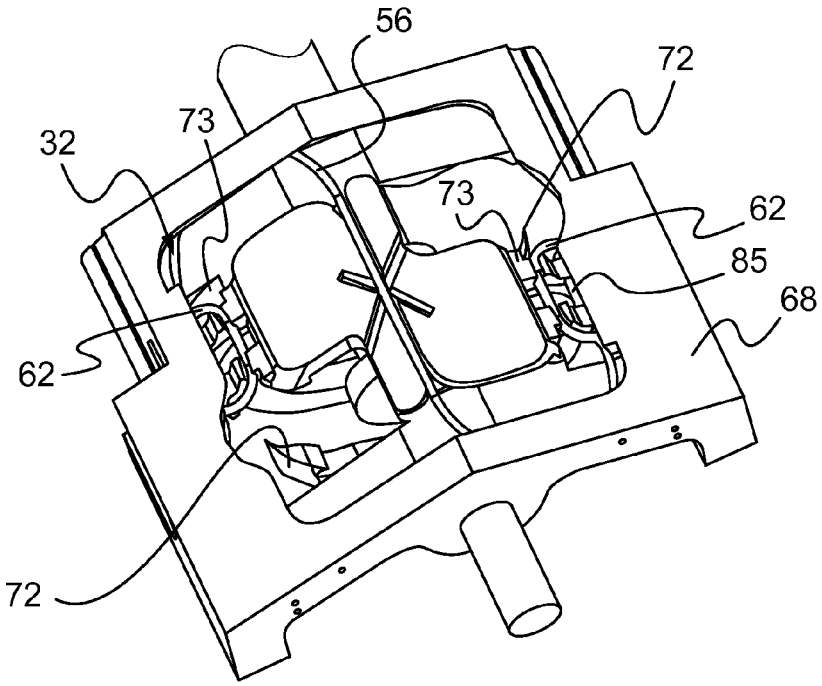
FIGS. 10A-10I are schematic views of slider plates configured to secure engagement between the needles and sutures.
Figure 10B:
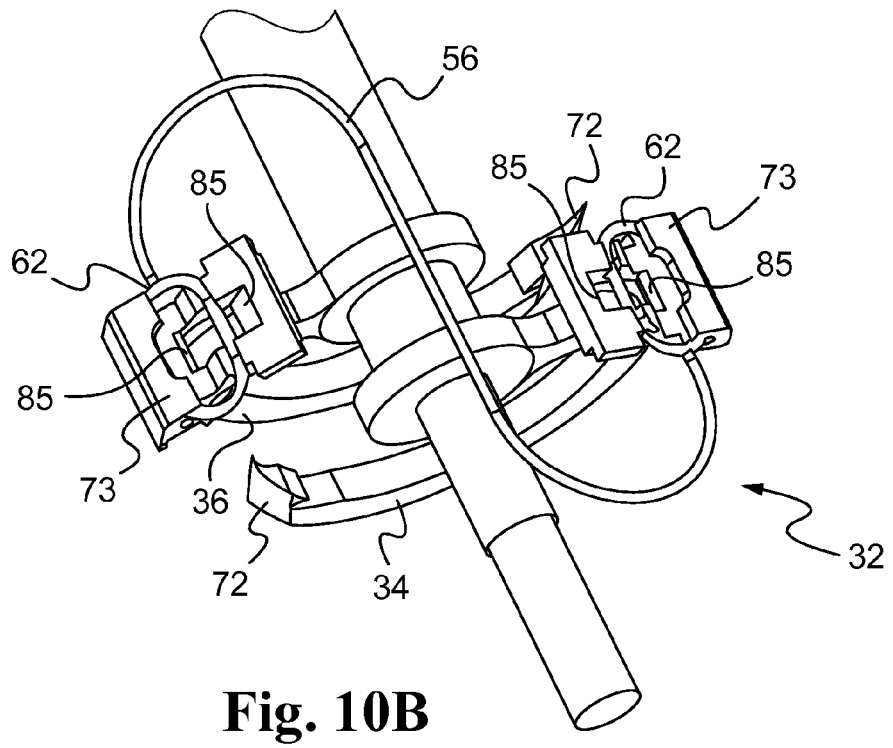
Figure 10C:
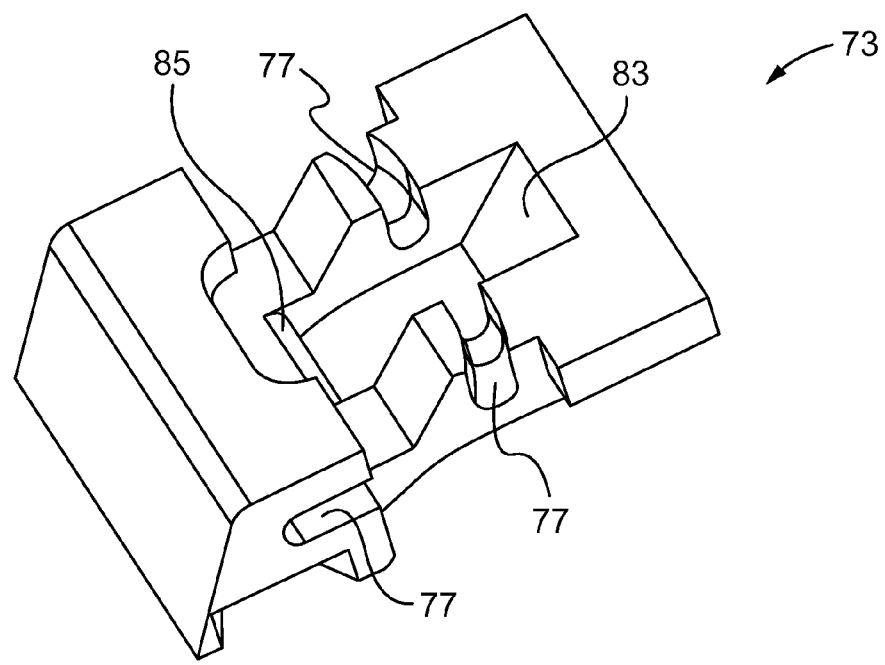
Figure 10D:
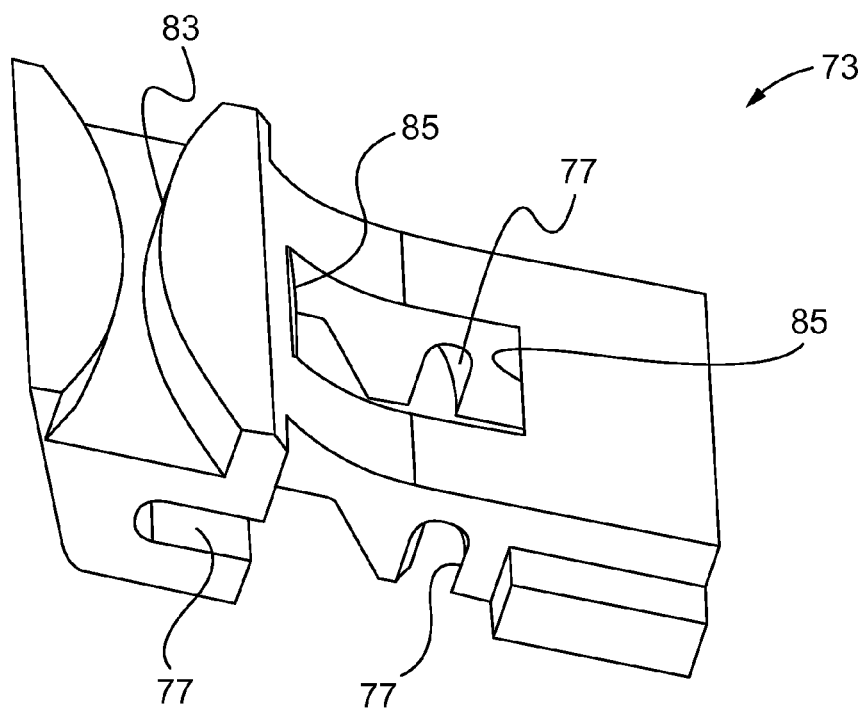

In order to secure the engagement between the suture 32 and the needle 34, 36 during deployment, slider plates 73 as shown in FIGS. 10A-10I, or the like, may be provided to temporarily hold and align each needle guide 62 along the rotational path of its corresponding needle 34, 36. Moreover, in the retrograde configuration of FIGS. 10A-10I, the slider plates 73 may be configured to enable the needles 34, 36 to pass through the needle guides 62 upon actuation of the suturing device 20 and securely seat the needle guides 62 in the corresponding recesses 74 of the needles 34, 36 upon release of the suturing device 20 and prior to deployment of the suture 32. As shown in FIGS. 10A-10B, the slider plates 73 may be slidably disposed within the cartridge 68 and shaped to receive the needle guide 62 of a suture 32 therein. As shown in FIG. 10C, each slider plate 73 may provide grooves 77 within which the needle guides 62 of the suture 32 are seated. While the embodiments of FIGS. 10A-10I are shown with looped needle guides 62, it should be understood that the slider plates 73 may be adapted to receive other needle guide designs as well.

The slider plates 73 may also be slidable relative to the cartridge 68 so as to enable the slider plates 73 to move in accordance with the rotation of the needles 34, 36. Additionally, as further disclosed in FIG. 10D, the slider plate 73 may include a recess 83 which slidably mates with the cartridge 68 to house a biasing mechanism. Moreover, the biasing mechanism may employ a spring, or the like, configured to bias the slider plates 73 in a substantially medial position, a lateral position, or any combination thereof, relative to the cartridge 68. The slider plates 73 may further comprise a cam slot 85 having surfaces which interface with the inner and/or outer edges of each needle 34, 36, and more particularly, with the needle tip 72 thereof. More specifically, the surfaces of the cam slot 85 may be sized, angled, and generally configured to abut the edges of each needle tip 72 as the needles 34, 36 are advanced therethrough and to secure engagement between the recesses 74 of the needles 34, 36 and the corresponding needle guides 62.

Figure 10E:
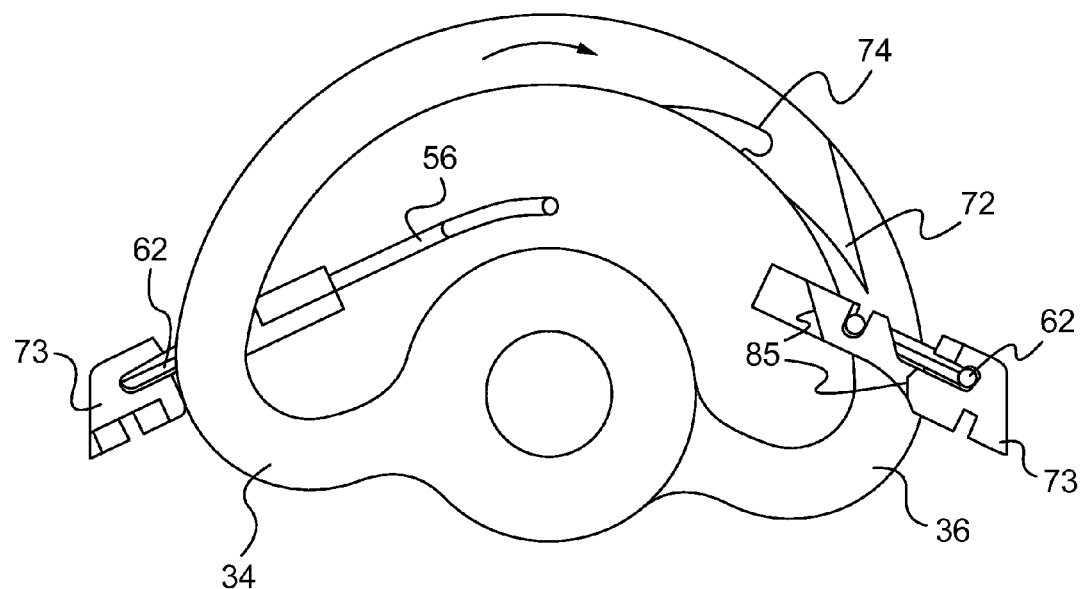
Figure 10F:
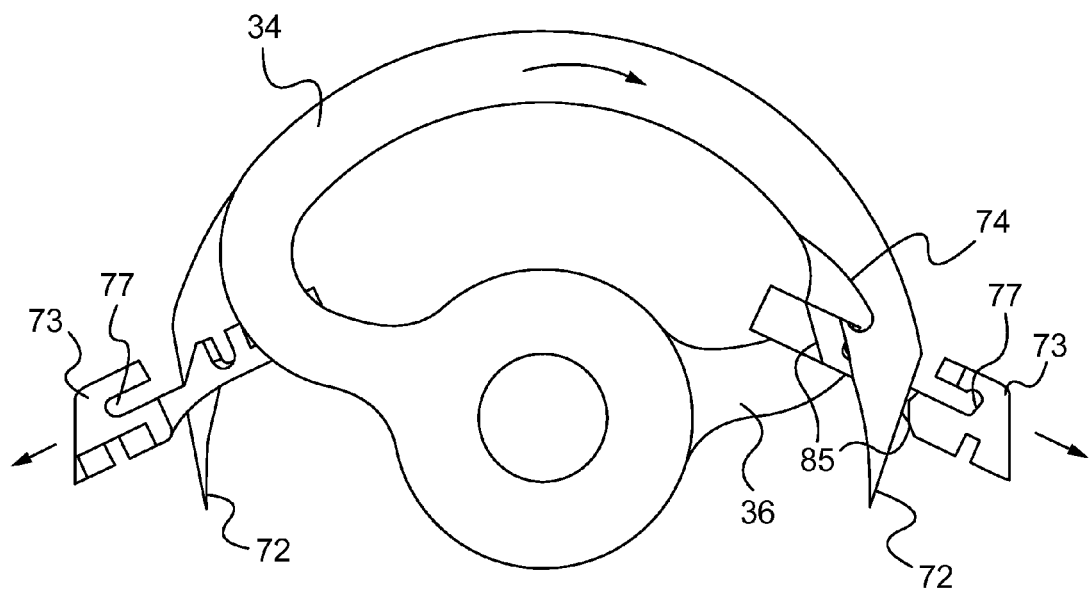
Figure 10G:
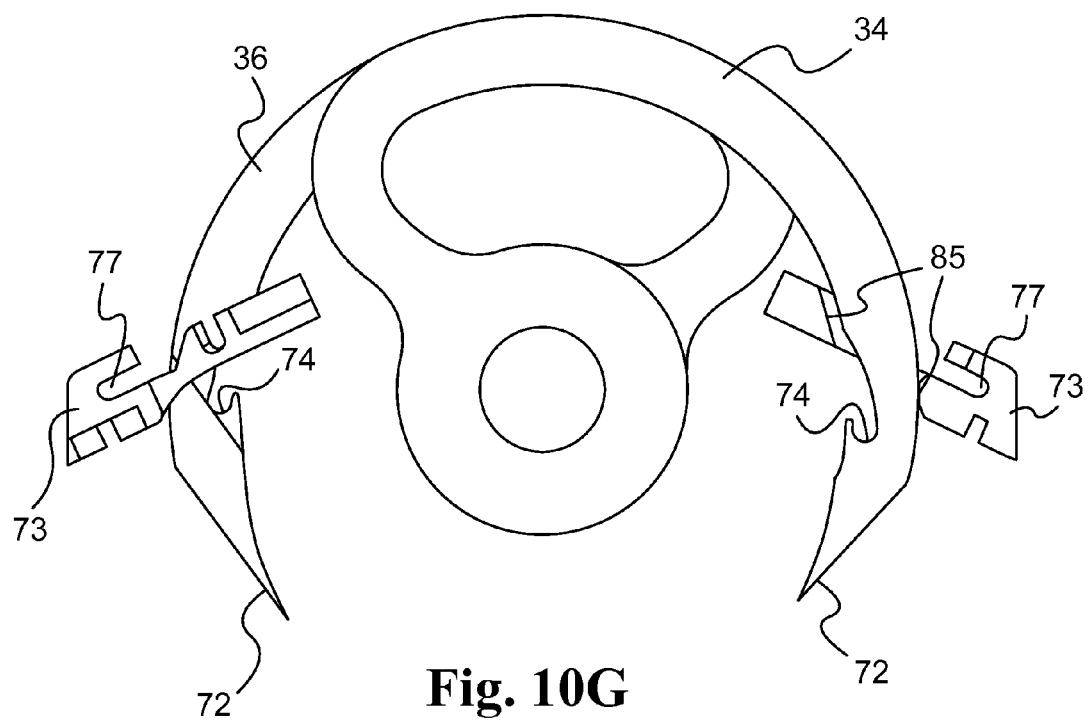
Figure 10H:
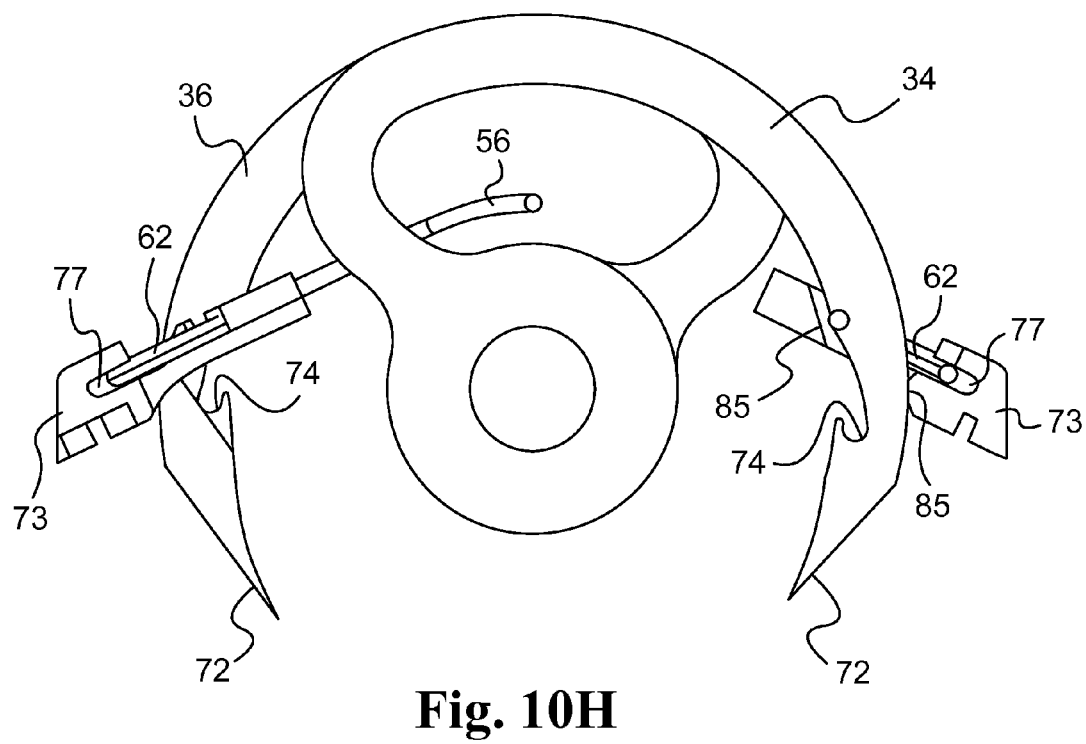
Figure 10I:
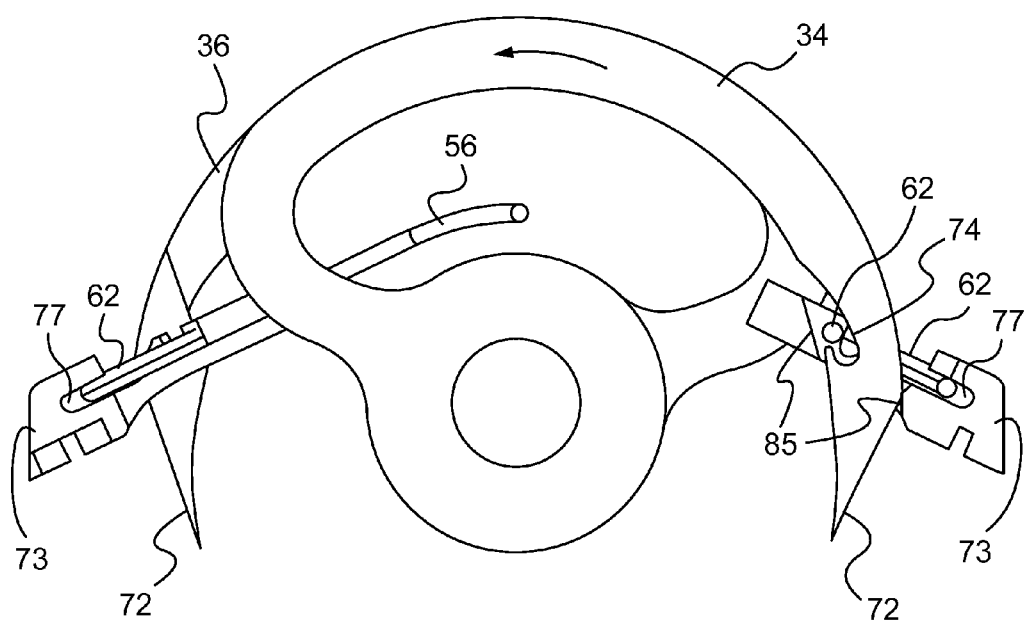

As shown in the retrograde application of FIGS. 10E-10F, for example, when the suturing device 20 is engaged and the needles 34, 36 are advanced, the outer edge of each needle tip 72 may push against the inwardly facing surfaces of the cam slots 85, causing the slider plates 73 to slide outwardly relative to the needles 34, 36 and the cartridge 68. Such outward motion of the slider plates 73 may be limited by the abutment between the outwardly facing surface of the clam slots 85 and the inner edge of the needles 34, 36, as shown for example in FIGS. 10G-10H. Biasing mechanisms disposed between the slider plates 73 and the cartridge 68 may also limit the outward motion of the slider plates 73 as the needles are advanced therethrough. As further depicted in FIG. 10I, when the suturing device 20 is disengaged and while the needles 34, 36 are refracted, the surfaces of the cam slot 85 may abut the inner and/or outer edges of the needles 34, 36 in a manner configured to secure the needle guide 62 within the needle recesses 74. Accordingly, it can be seen that the slider plates 73 enable the needles 34, 36 to substantially freely pass therethrough while conforming to the shape and movement of the needles 34, 36 so as to ensure that each needle guide 62 is securely held by the respective needles 34, 36 prior to and during deployment. It should be understood that the slider plates 73 may be similarly adapted for antegrade configurations employing needles 34, 36 with recesses 74 configured to engage with needles guides 62 upon advancement rather than retraction.

Turning now to FIGS. 11A-11J, alternative embodiments for the suture 32 which can be used in conjunction with the teachings of the present disclosure are disclosed. For example, while FIGS. 1-9 depict the suture 32 with a smooth filament 56, FIGS. 11A-11F depict sutures 32 with multiple tines 76 or other elements radially and outwardly extending from the cylindrical filament 56. As will be noted, in some embodiments, the elements 76 all extend in the same direction, while in other embodiments, they extend in opposite directions. The elements 76 may be canted in one direction to facilitate insertion in that direction, but hinder removal in the opposite direction. For example, the elements or tines 76, as depicted in FIGS. 11A-11F, may also be provided in the substantial shape of spheres, cones, pyramids, fins, or any other two- or three-dimensional structures having canted sides 78 adapted to facilitate insertion of the suture 32 through the tissue of the skin while enabling the skin to cam thereagainst. Furthermore, the elements or tines 76 may be formed using a combination of different shapes, for example, as shown by the finned, cone-type retention elements 76 of FIG. 11E. Not only do the tines 76 serve as frictional interference devices to better grip the first and second sections of skin once installed, but given the orientation which the suture 32 ultimately assumes upon insertion, the tines 76 can actually interlock so as to form an even tighter closure, and avoid retraction and medialization as will be described in further detail herein. Moreover, as shown in FIGS. 12A-12B, such tines 76 prevent medialization and refraction. As used herein, retraction refers to the tines preventing reverse movement of the suture out of the skin or away from the intersecting portion on the suture after installation and medialization refers to laterally inward sliding of the suture past a central portion of the suture after being installed in the closed helical configuration of FIG. 12A.

Figure 11A:
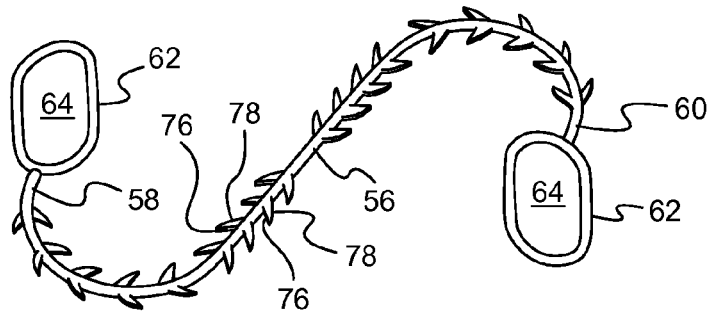
Figure 11B:
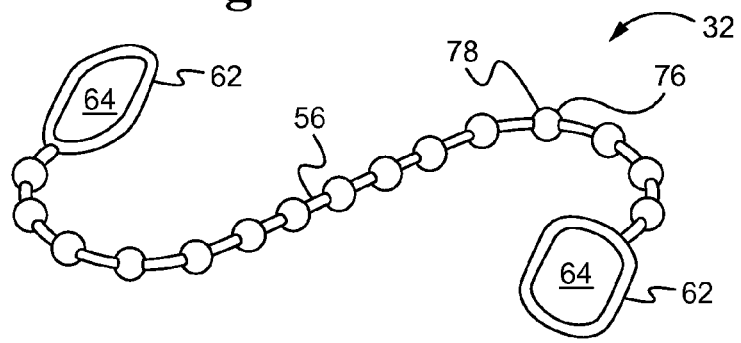
Figure 11C:
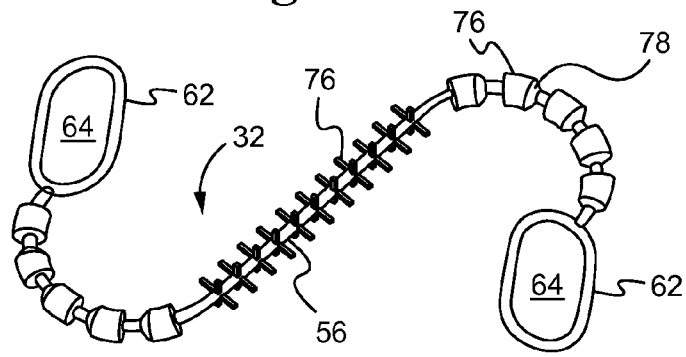
Figure 11D:
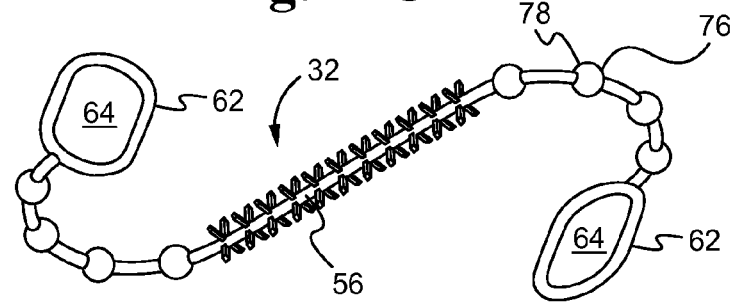
Figure 11I:
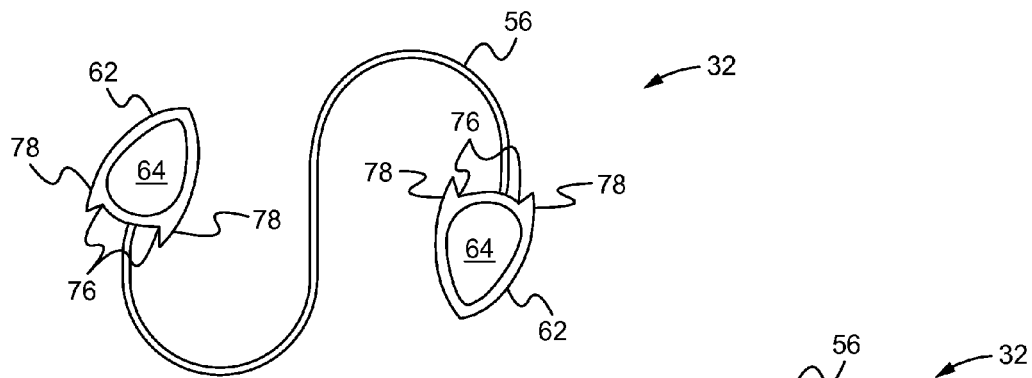
Figure 11J:
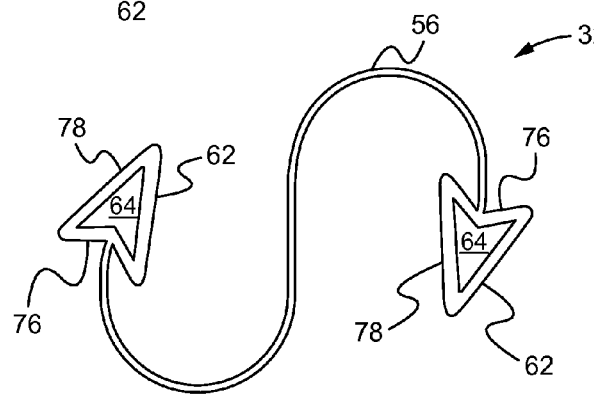
Figure 12A:
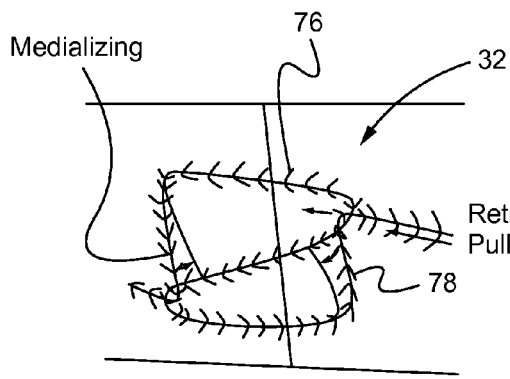
FIGS. 12A-12B are schematic views of a suture pre-insertion and post-insertion depicting how outwardly extending elements of the suture avoid medialization and retraction.
Figure 12B:
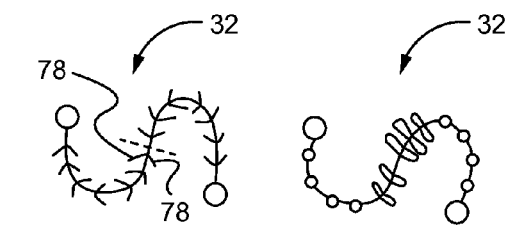

With particular reference to FIGS. 11G-11J, further alternative embodiments for the suture 32 can be implemented in accordance with the teachings of the present disclosure. In contrast to the sutures 32 of FIGS. 11A-11F in which tines 76 and/or canted elements 78 were disposed on the filament 56, the sutures 32 of FIGS. 11G-11J provide substantially smooth filaments 56 and instead provide tines 76 and/or canted elements 78 directly on the needle guides 62. As with previous embodiments, the sutures 32 of FIGS. 11G-11J are similarly configured to facilitate insertion of the ends of the suture 32 in a corresponding direction while hindering removal in an opposing direction. More specifically, each needle guide 62 may be configured to at least partially collapse upon insertion so as to minimize physical resistance with the skin, but expandable when pulled in an opposing direction so as to maximize resistance and hinder removal thereof. Additionally or optionally, each end of the suture 32 may have more than one needle guide 62 as shown in phantom lines in FIG. 11G so as to further hinder removal from the skin once inserted. While the tip of each needle guide 62 in FIG. 11G is rounded, alternative modifications may employ needle guides 62 with more canted or sharper tips to further facilitate insertion thereof as depicted in FIGS. 11H-11J. Moreover, the needle guides 62 can generally be formed in the shape of a loop, circle, ellipse, oval, square, triangle, polygon, or any other suitable shape which at least marginally facilitates insertion thereof into skin but hinders removal. The needle guides 62 may additionally be formed as a simple thickening without an aperture that is sized and configured to be engaged by the recesses 74 of the first and second needles 34, 36 during insertion into the skin, as well as to prevent retraction from the tissue once deployed. Furthermore, with any of the foregoing types of sutures, the device 20 may include a magazine (not shown) of sutures so as to advance each into successive position automatically after installation of the preceding suture.

Figure 14:
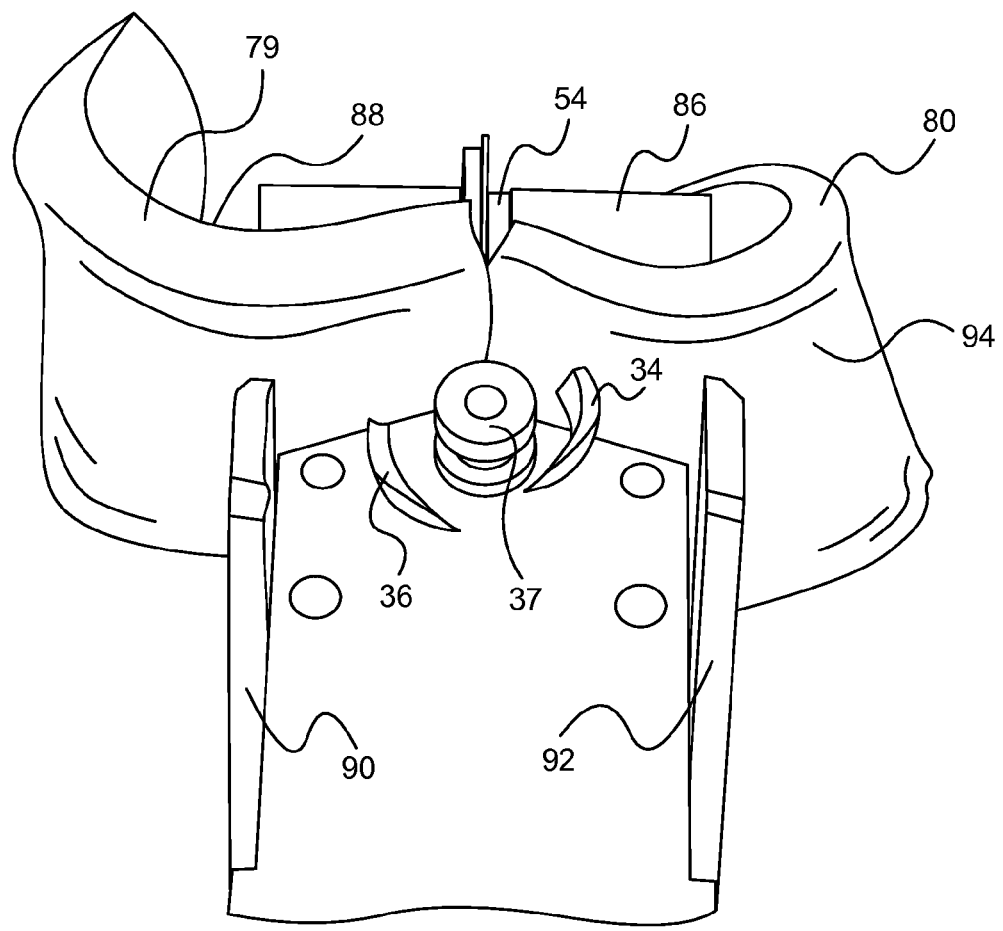
FIG. 14 is a bottom perspective view of the test fixture version of suturing device of FIG. 13.
Figures 15A, 15B, 15C, 15D, 15E:
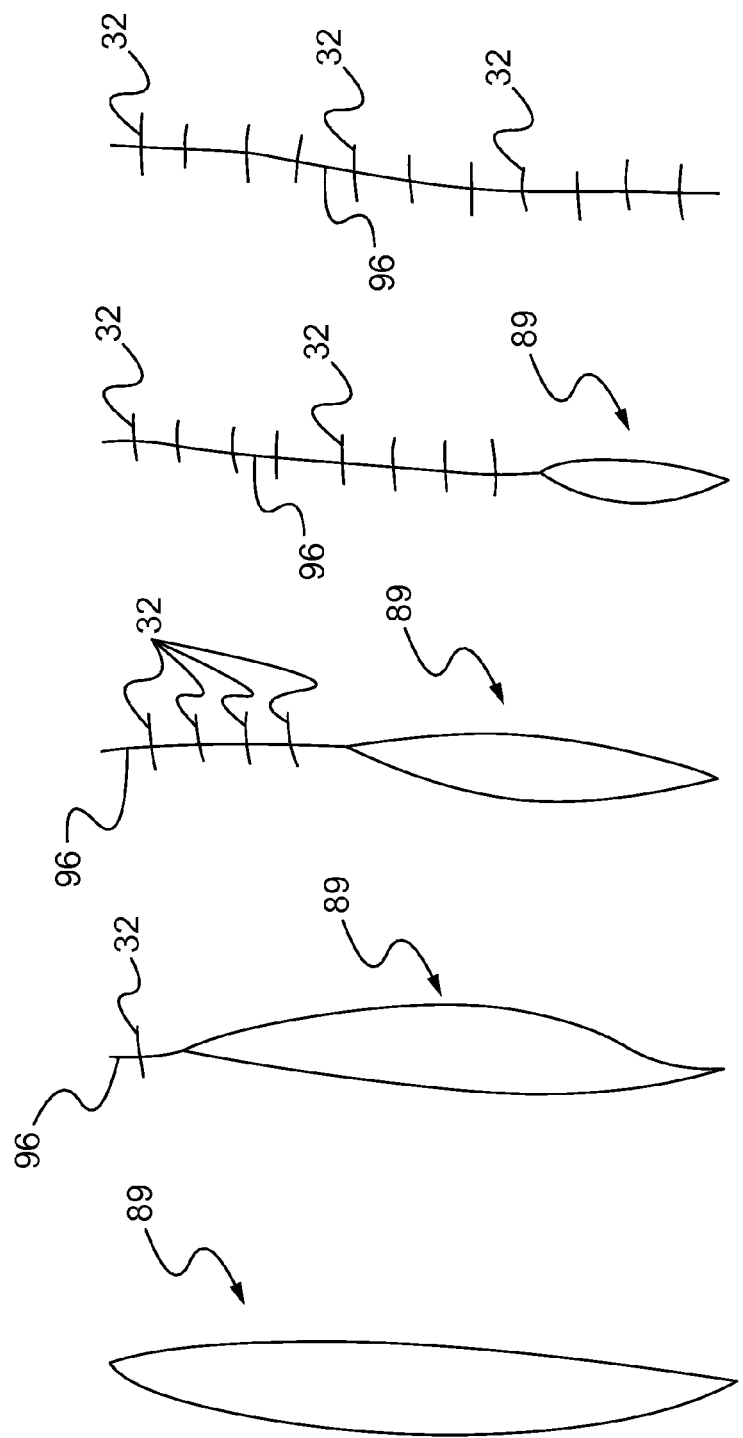
FIGS. 15A-15E depict plan views of an incision at various stages after the suturing tool of the present disclosure has been used.

In operation, the suturing device 20 can be used to quickly and effectively close an incision in human skin with precise alignment of the sections of skin to be closed, close approximation of the closure edges, and minimal scarring. With reference to FIGS. 13-14, first and second sections of skin 79, 80 are shown inserted into the first and second guide channels 82, 84 of a test fixture 86 constructed in accordance with the teachings of this disclosure. Of course, for complete disclosure, it should be noted that FIGS. 13-14 are simply a depiction of a test version of the suturing device 20 completing a closure in accordance with a sample of skin. In actual operation, an incision may be provided somewhere within the human body, and the operating end 30 may be positioned under the skin relative to the incision such that the skin sections 79, 80 are received in the guides channels 50, 52, and the sub-dermal side of the skin sections 79, 80 may rest on the serrations 75 of the cartridge frame 71. In one of the several possible methods of using the suturing device 20, the suturing device 20 may initiate its operation at one end of the incision 89, install a suture 32, and then longitudinally retract along the closure until the next suture is inserted and so on. This process would continue until the incision is completely closed as depicted in FIGS. 15A-15E. Additionally, first and second restraining jaws 90, 92 may be provided which, when rotated upwardly, are configured to engage the sub-dermal layer 94 of the skin sections 79, 80. The restraining jaws 90, 92 may be omitted or added as an optional feature in certain embodiments, such as in the embodiment of FIGS. 1-9 which has serrations 75 configured to serve essentially the same purpose.

In an alternative method of use, for example, the suturing device 20 may initiate its operation and install a suture 32 substantially at the middle of the incision 89 so as to segment the incision 89 into two halves. Subsequent sutures 32 may be installed in a similar manner and positioned so as to further segment each remaining half of the incision 89 into two smaller halves, and so forth, until the incision 89 is completely closed. In a still further method, the suturing device 20 may be used to install sutures 32 beginning at the ends of the incision 89 until the sutures 32 meet at the middle to completely close the incision 89. Further alternative methods of using the suturing device 20 will be apparent to those skilled in the art.

Still referring to FIGS. 13 and 14, when the trigger 26 of the suturing device 20 is compressed toward the handle 24, the first and second arcuate needles 34, 36 rotate and thereby insert themselves through the dermal layer 94 of the first and second sections of skin 79, 80, respectively. In so doing, using a pair of needles 34, 36 as configured in FIG. 9A, suture 32 can be installed in a retrograde fashion in that the first and second arcuate needles 34, 36 can be fully rotated, and then only after being fully rotated, will both needle guides 62 of the suture 32 be captured and, upon retraction of the needles 34, 36 and release of the suturing device 20, pulled through the respective skin sections 79, 80 in opposite directions. Conversely, using a pair of needles 34, 36 as configured in FIG. 9B, the suture 32 can be pushed in an antegrade manner by the needle guide 62 through the section of skin which it first enters, cross over interface 96 between the first and second sections of skin 79, 80 and into the second section of skin. In either the antegrade or the retrograde configuration, as both needles 34, 36 are simultaneously moving and rotating substantially equal distances, both needle guides 62 are being so pushed or pulled in opposing directions. In alternative embodiments, each needle 34, 36 may be rotated substantially equal distances but at unequal rates of angular displacement.

Figure 16A:
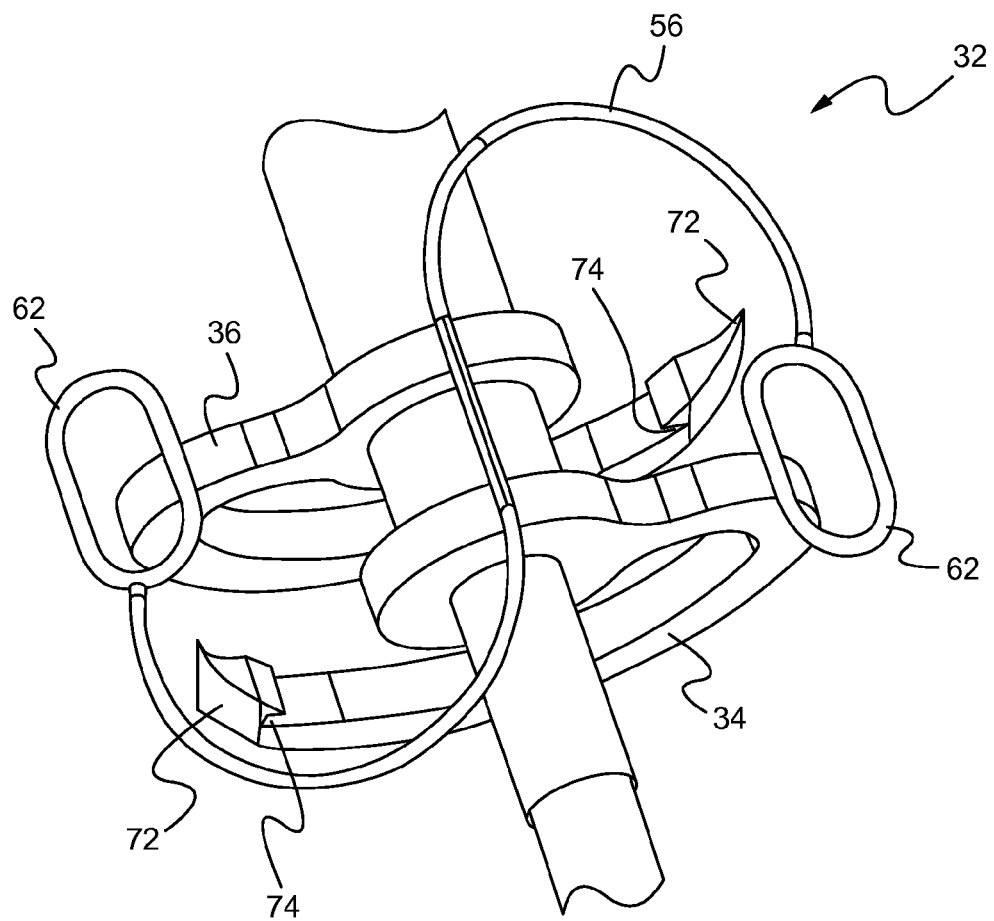
FIGS. 16A-16F are schematic representations of the suture pre-insertion when the closed helix configuration of the technology is used.

Using either an antegrade or a retrograde suturing scheme, after installation of the suture 32, the needles 34, 36 will have pierced both sections of skin 79, 80, and the suture 32 will be transformed from a planar, bi-planar, multi-planar, or any other non-helical configuration to a substantially helical configuration. Furthermore, using either one of the antegrade or the retrograde configuration, the suturing device 20 may be adapted to form a closed helix or an open helix simply by adjusting the starting position of the suture 32 relative to the needles 34, 36. As shown in FIGS. 16A-16N, for example, a single suturing device 20 used in the retrograde configuration can form both closed helix and open helix closures using identical sutures 32 simply by adjusting the starting position of the suture 32 placed thereon prior to engaging the suturing device 20. Although not shown, a single suturing device 20 used in the antegrade configuration can similarly be used to form both closed helix and open helix closures using identical sutures 32 simply by adjusting the starting position of the suture 32 placed thereon prior to engaging the suturing device 20.

Figure 16B:
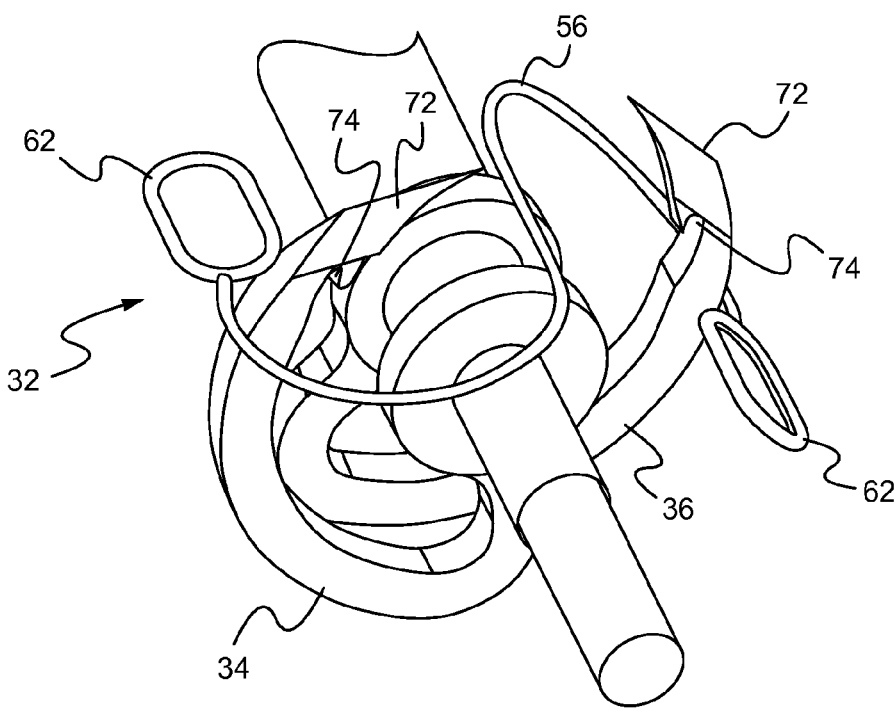
Figure 16C:
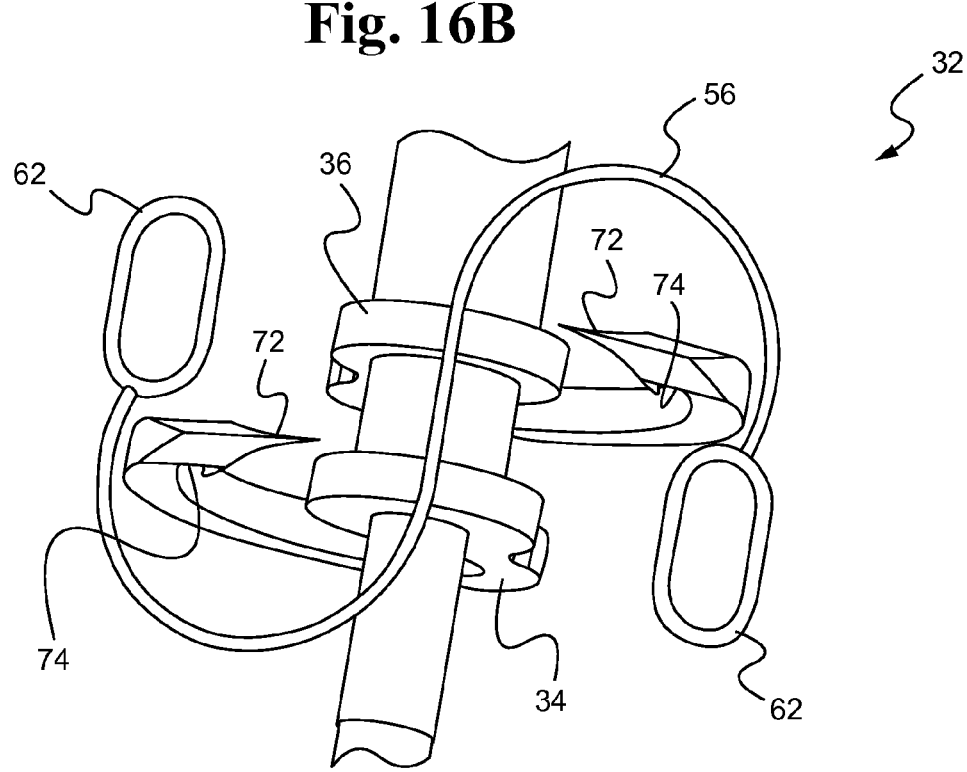
Figure 16D:
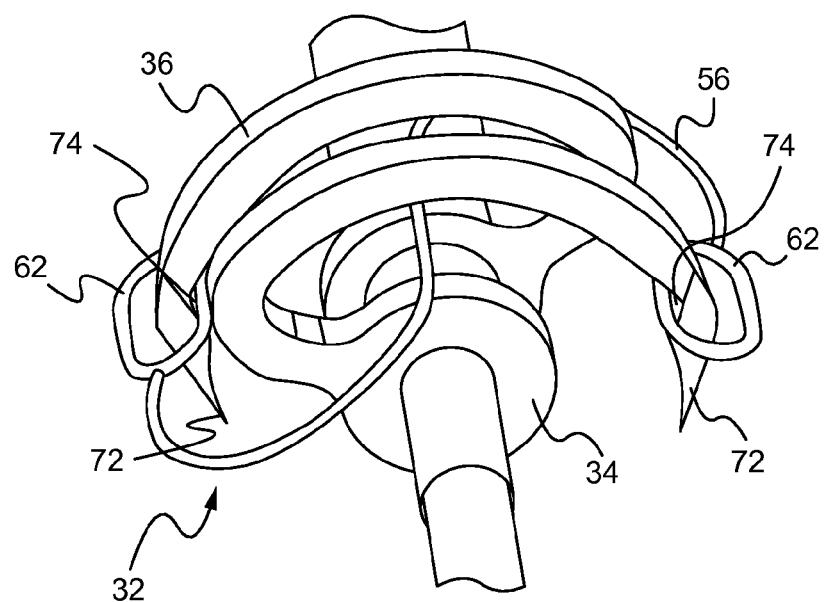
Figure 16E:
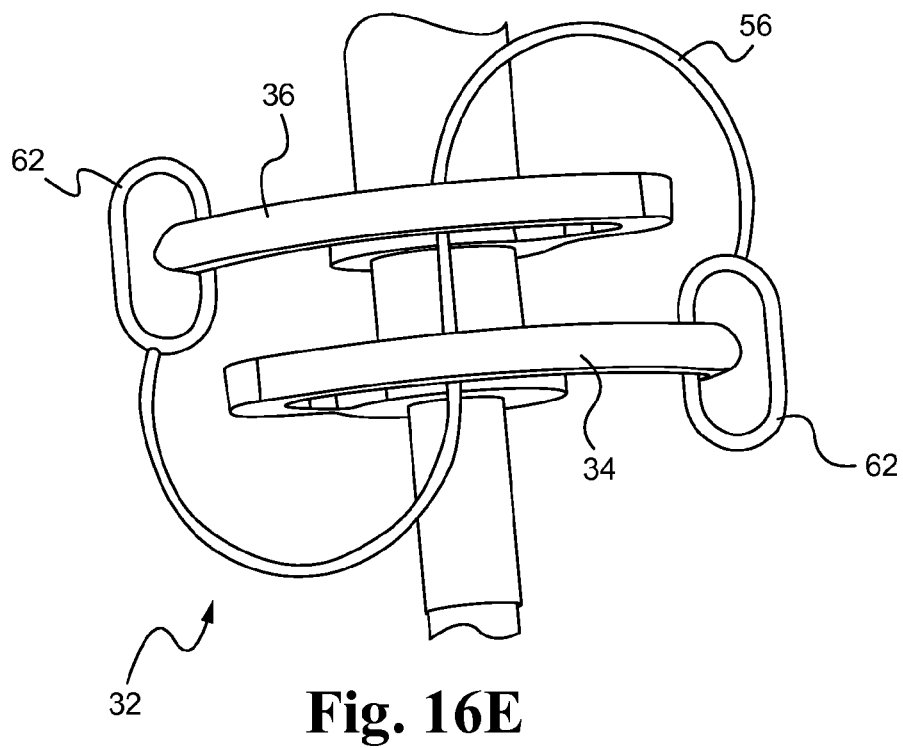
Figure 16F:
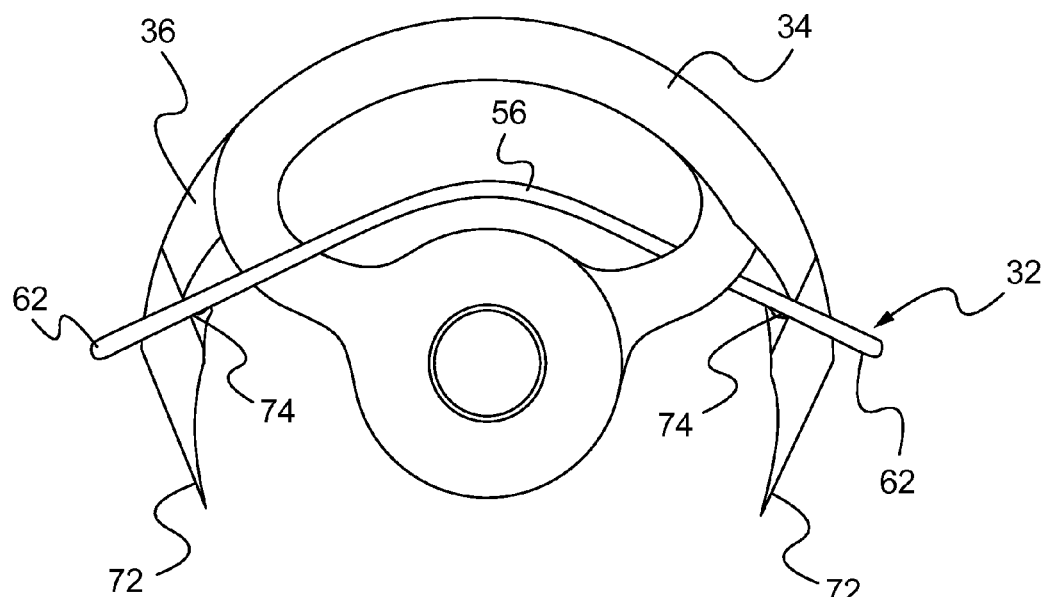
Figure 16G:
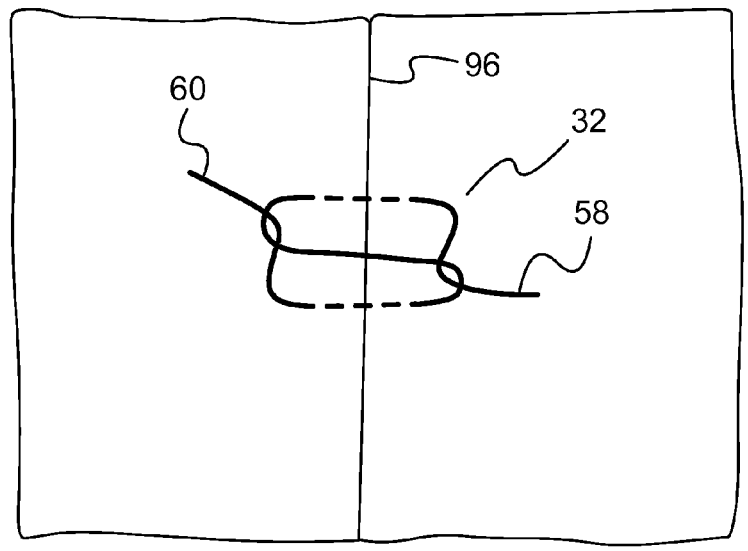
FIG. 16G is a schematic representation of the suture post-insertion as viewed from the deep skin surface when the closed helix configuration of the technology is used.

With particular reference to FIGS. 16A-16G, the retrograde suturing device 20 can be used to form closed helix closures by setting the suture 32 in the starting position shown in FIG. 16A. In the starting position shown, the suture 32 is positioned such that each needle guide 62 thereof is adapted to receive its corresponding needle 34, 36 and be engaged by the recess 74 of the needle 34, 36 upon compression of the suturing device 20. Moreover, in order to form a closed helix closure, the filament 56 of the suture 32 is routed around the outside of and between the needle tips 72, as shown in FIG. 16A. As the suturing device 20 is engaged, each needle tip 72 may rotate toward its corresponding needle guide 62, as shown in FIGS. 16B-16C, until the recesses 74 engage both needle guides 62, as shown in FIGS. 16D-16F. Once each needle guide 62 is engaged, release of the suturing device 20 may pull the needles guides 62 through the skin in retrograde fashion until a closed helix or a closed helical knot-like configuration is formed, as shown in FIG. 16G.

Figure 16H:
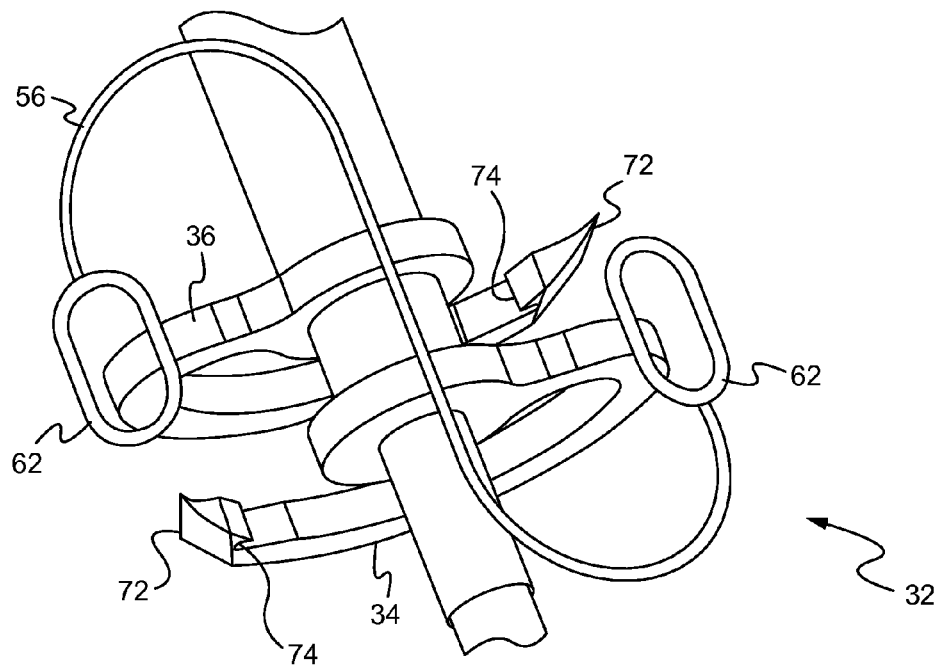
FIGS. 16H-16M are schematic representations of the suture pre-insertion when the open helix configuration of the technology is used.
Figure 16I:
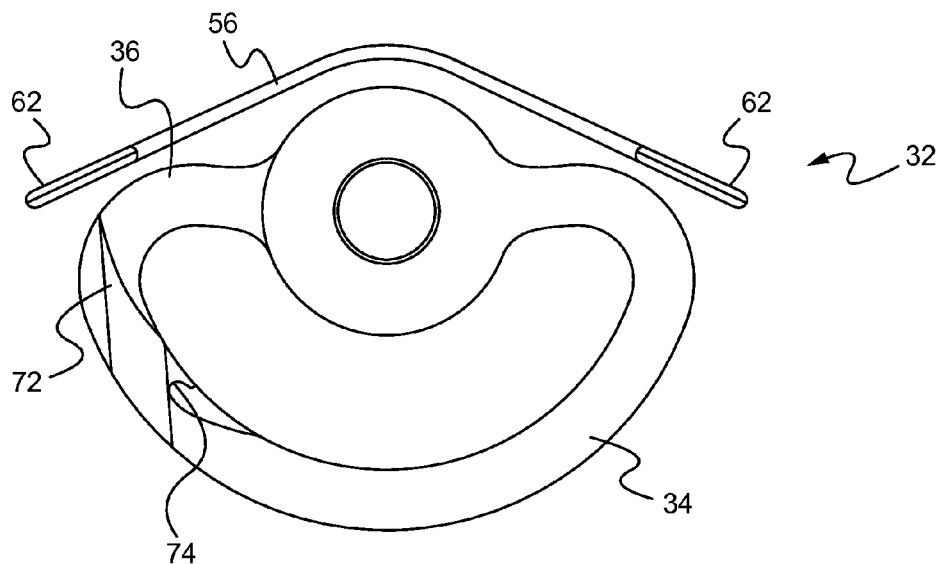
Figure 16J:
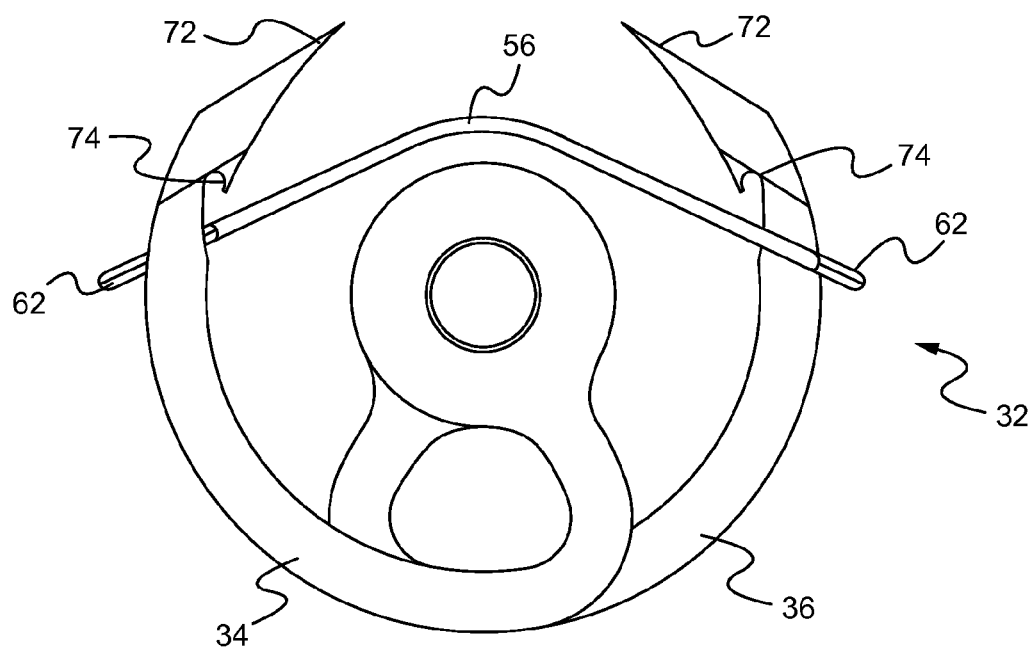
Figure 16K:
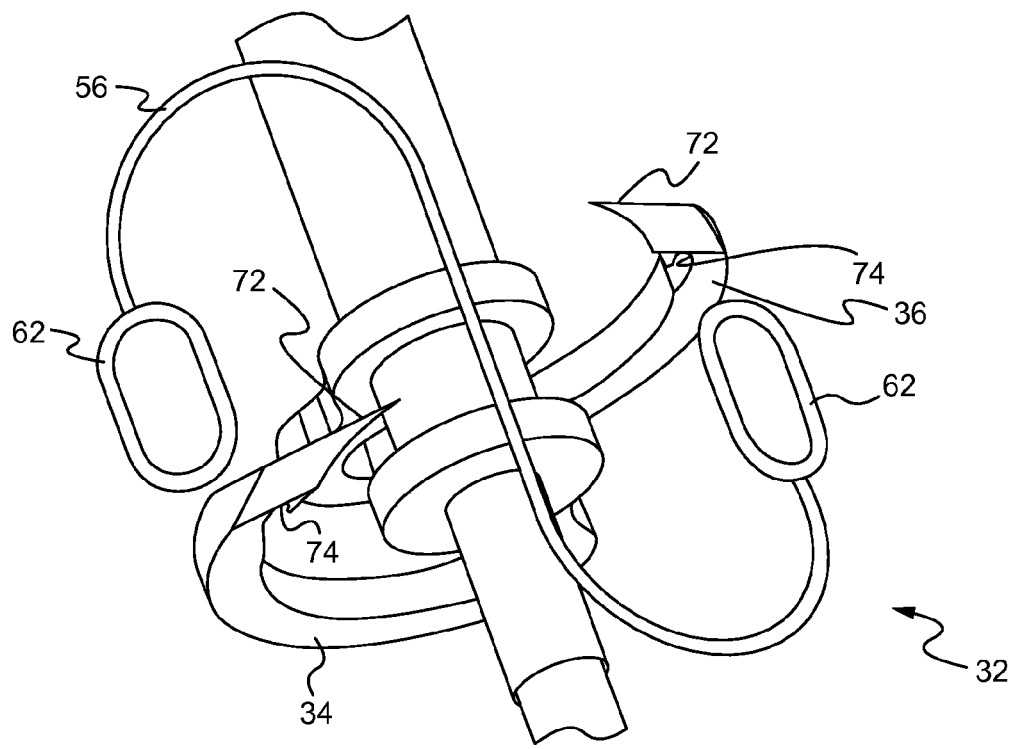
Figure 16L:
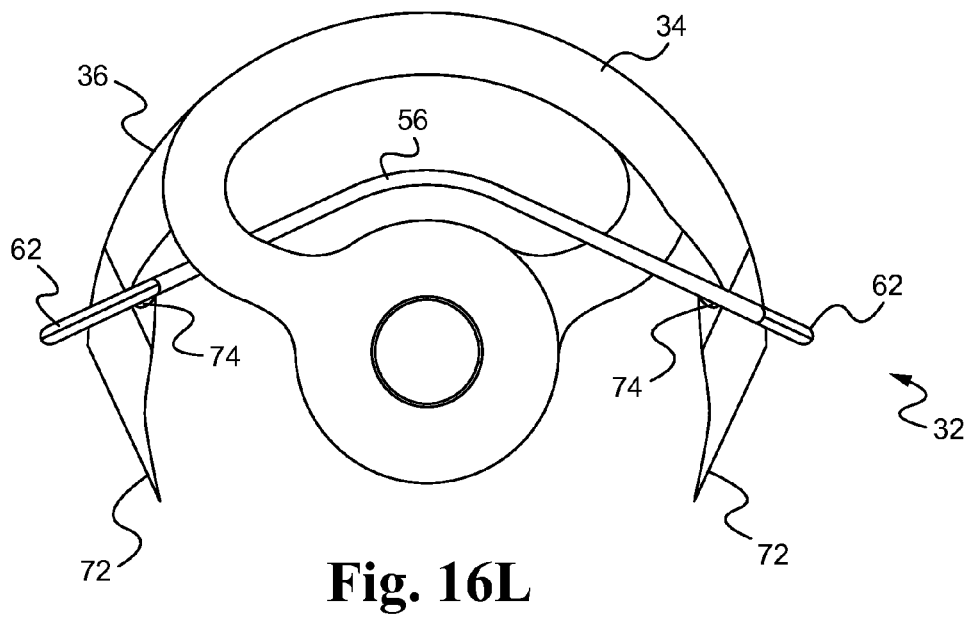
Figure 16M:
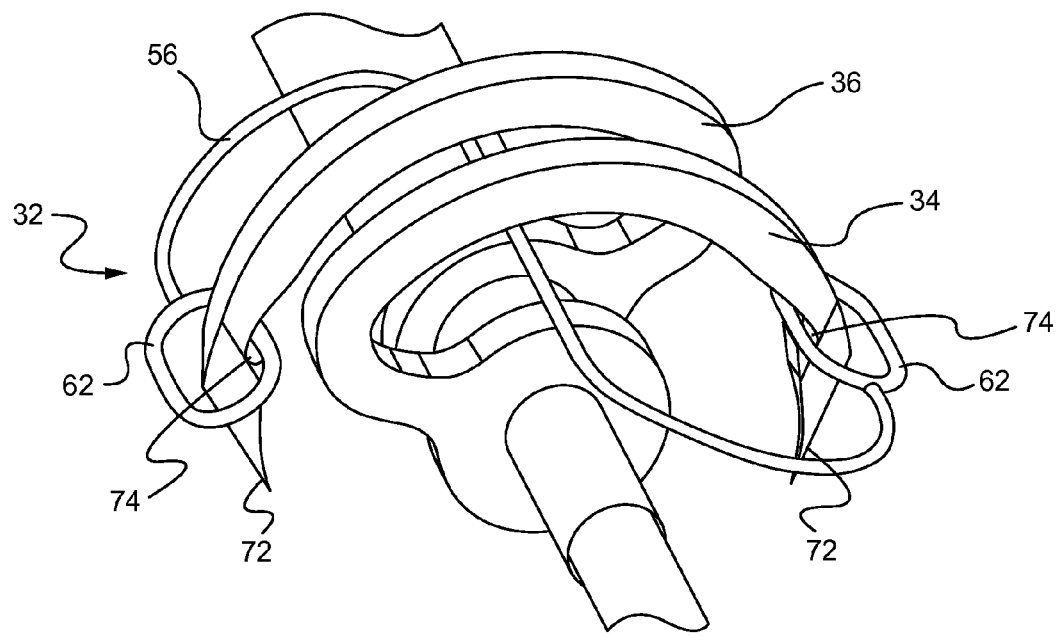
Figure 16N:
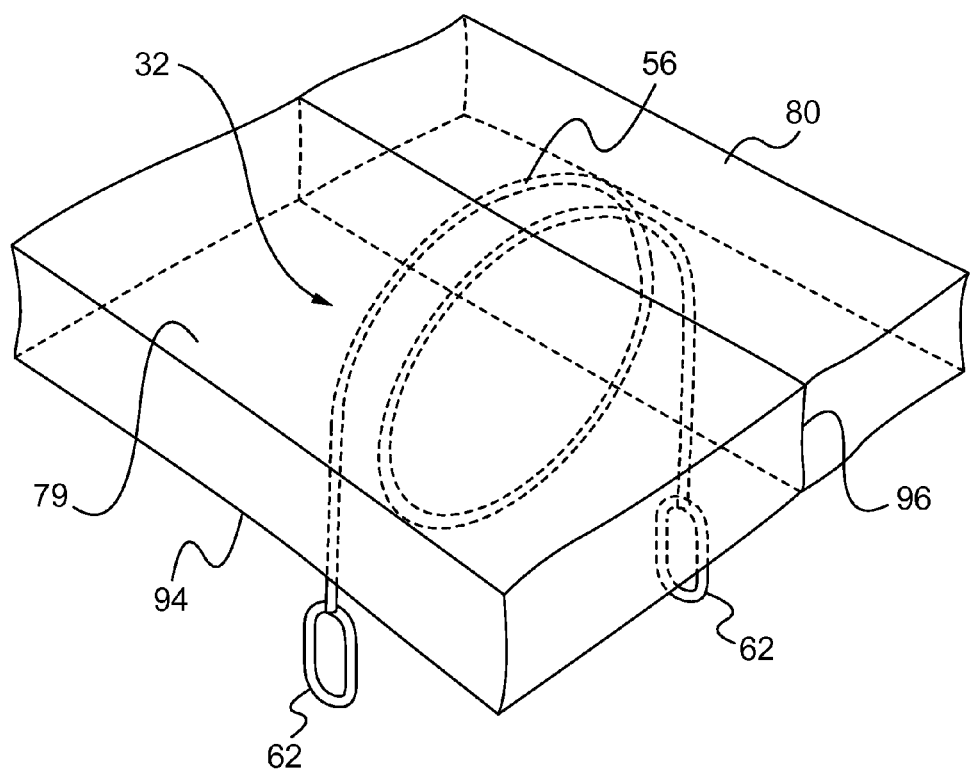
FIG. 16N is a schematic representation of an oblique view of the suture post-insertion as viewed from the superficial skin surface when the open helix configuration of the technology is used.

Turning now to FIGS. 16H-16N, the retrograde suturing device 20 can also be used to form open helix closures by setting the suture 32 in the starting position shown in FIG. 16H. In the starting position shown, and similar to the closed helix starting position of FIG. 16A, the suture 32 is positioned such that each needle guide 62 thereof is adapted to receive its corresponding needle 34, 36 and be engaged by the recess 74 of the needle 34, 36 upon compression of the suturing device 20. To form an open helix closure, the filament 56 of the suture 32 is routed away from but still between each needle tip 72, as shown in FIG. 16H. As the suturing device 20 is engaged, each needle tip 72 may rotate toward its corresponding needle guide 62, as shown in FIGS. 16I-16K, until the recesses 74 engage both needle guides 62, as shown in FIGS. 16L-16M. Once each needle guide 62 is engaged, release of the suturing device 20 may pull the needles guides 62 through the skin in retrograde fashion until an open helix configuration is formed, as shown in FIG. 16N.

Figure 17:
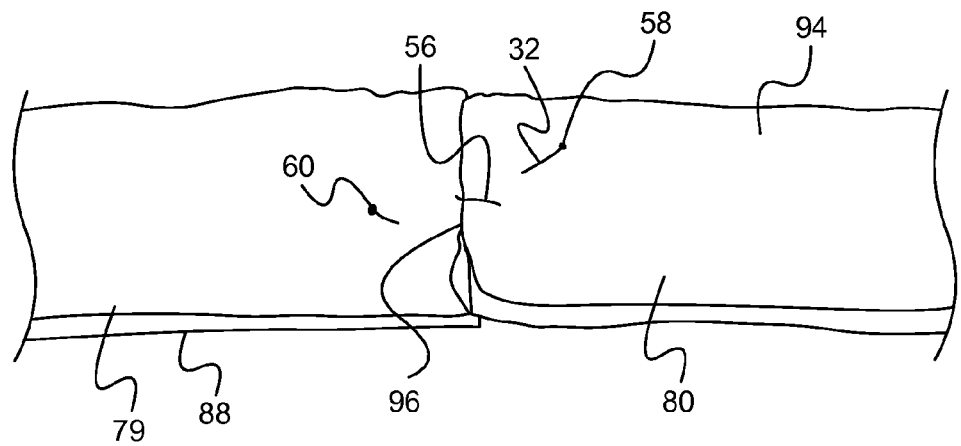
FIG. 17 is a perspective view (from the bottom/sub-dermal/undersurface) of the skin sections sutured together in open helix configuration in accordance with the teachings of the disclosure.
Figure 18:
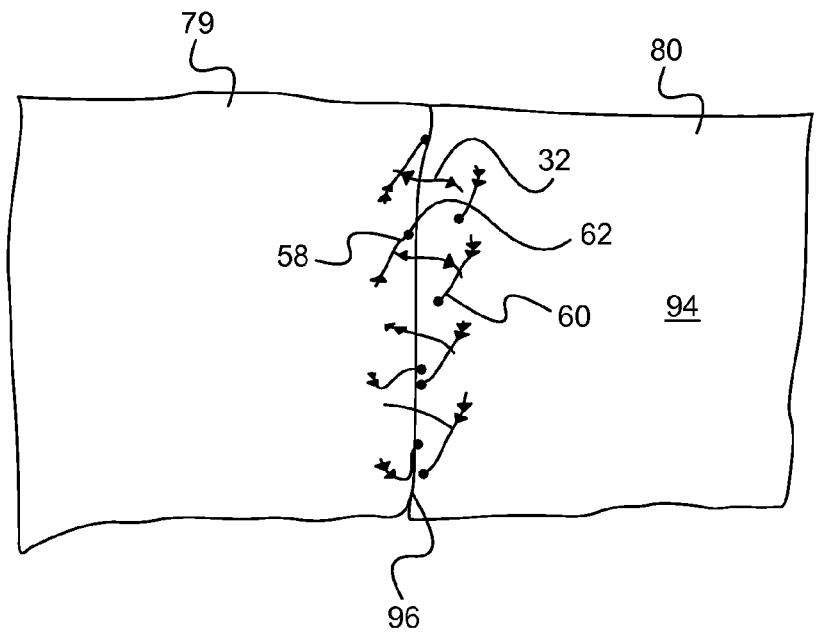
FIG. 18 is a plan view of two other sections of skin after being sutured by the present disclosure and showing the specific shape and position of multiple sutures after insertion in open helix configuration.
Figure 19:
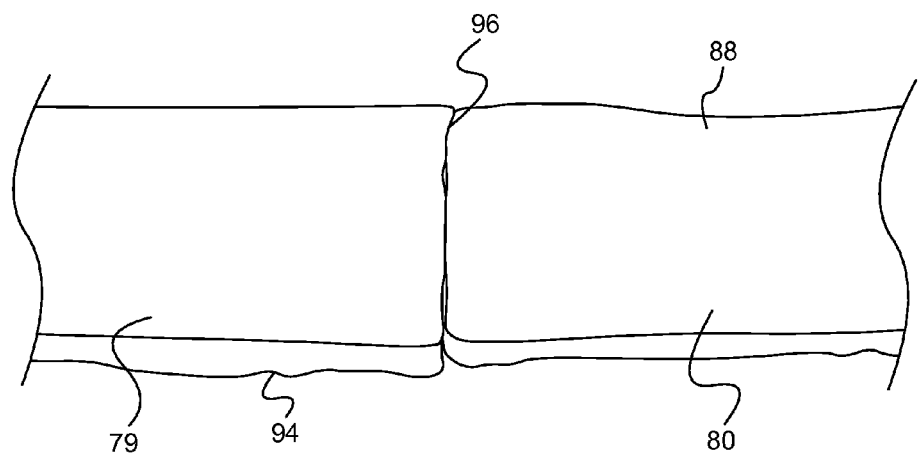
FIG. 19 is a perspective view of the superficial/exterior skin surface of FIG. 17.

The embodiments of FIGS. 17-18 depict similar open helical fastener configurations that are inserted into exemplary wounds. For example, FIG. 17 shows the dermal layer 94 of the first and second sections of skin 79, 80 after suture insertion with the filament 56 traversing through the first and second sections of skin 79, 80 and across the interface 96, with the first and second ends 58 and 60 of the filament 56 outwardly extending away from the dermal layer 94. The closure of FIG. 18 is very similar to FIG. 17 but simply shows a plurality of such sutures after installation. Perhaps most importantly, FIG. 19 shows the exterior or epidermal layer 88 of the first and second sections of skin 79, 80 after suture insertion. As shown therein, the first and second sections of skin 79, 80 are horizontally aligned such that the interface 96 is linear and tightly grouped. In addition, the first and second sections of skin 79, 80 are vertically aligned so as to be positioned within the same plane. This is effectively illustrated in a comparison of FIGS. 20A-20C.

Figures 20A, 20B, 20C:
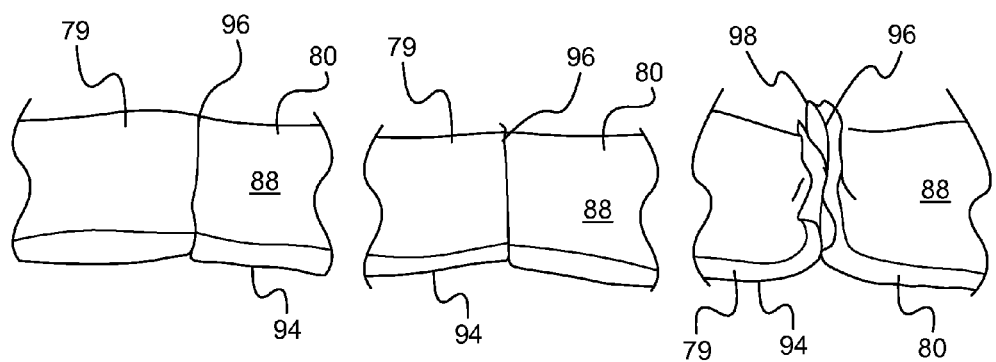
FIGS. 20A-20C are perspective views of prior art closure devices in comparison to the closure device of the present disclosure.
Figure 21:
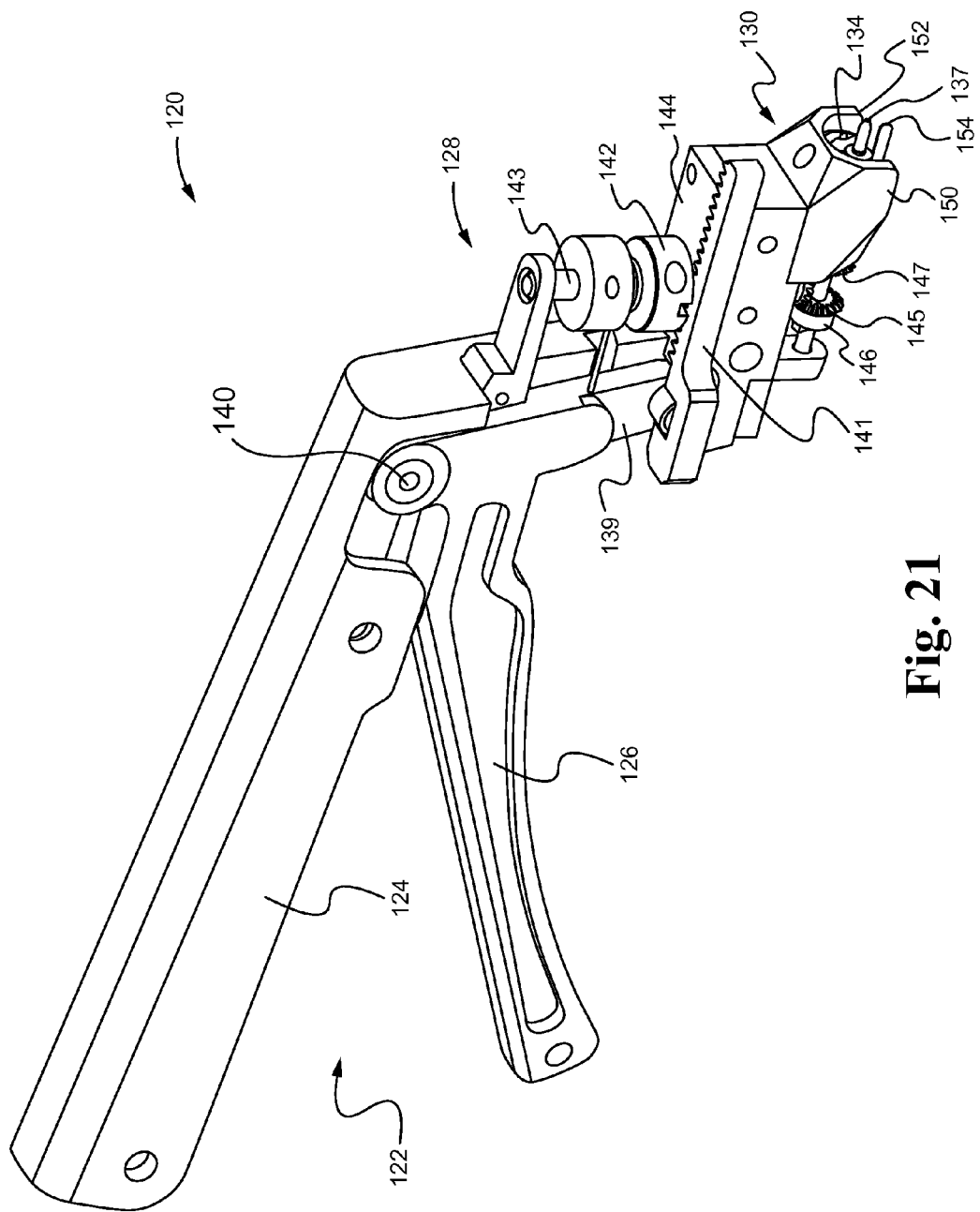
FIG. 21 is a perspective view of an alternative embodiment of a suturing tool constructed in accordance with the teachings of the disclosure and adapted to interface with the epidermal layer of skin, wherein the suture and cartridge (e.g., the alternate version of FIG. 8) have been removed for illustration purposes.
Figure 22:
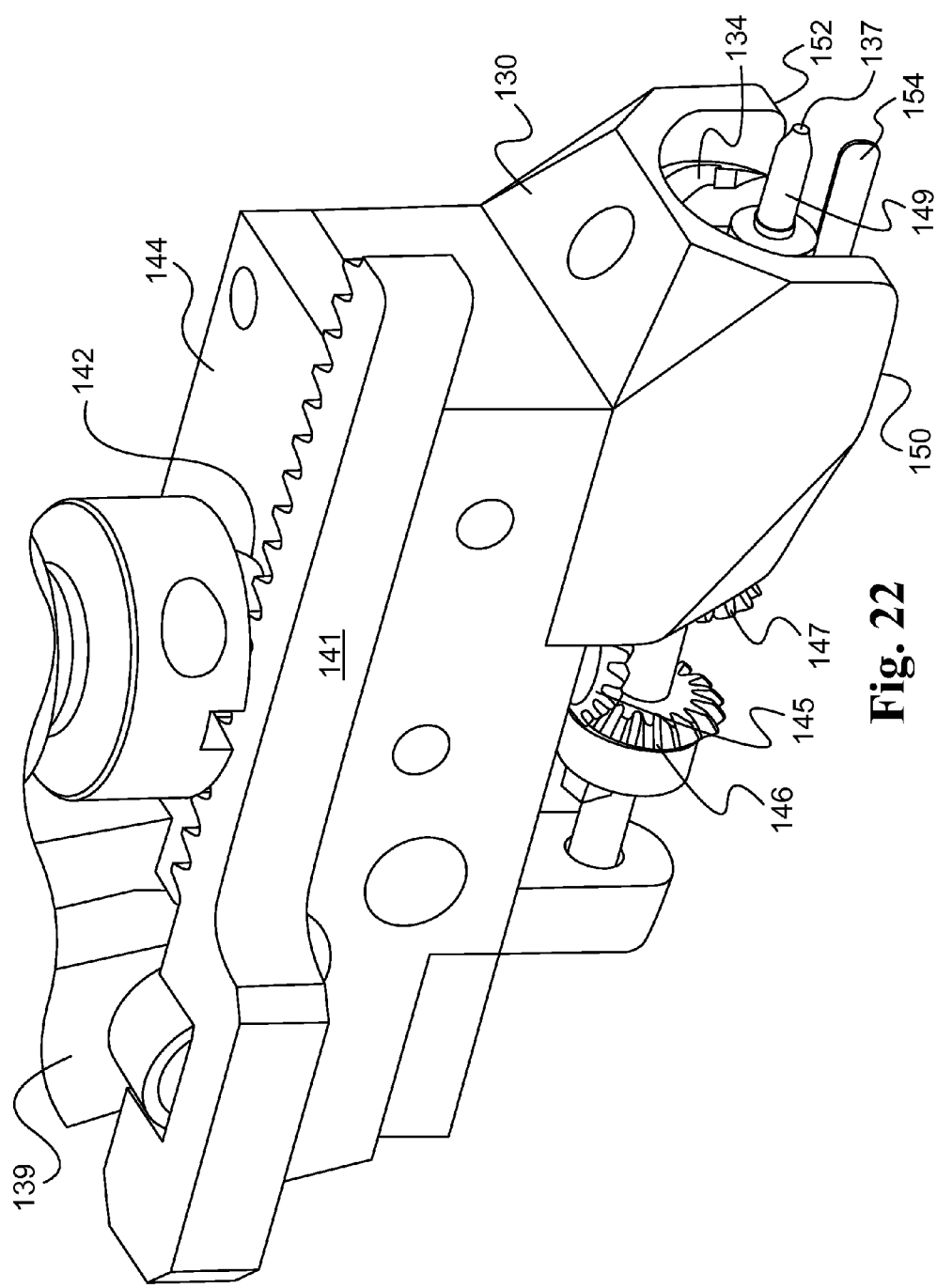
FIG. 22 is an enlarged perspective view of the operating end of the suturing tool depicted in FIG. 21.
Figure 23:
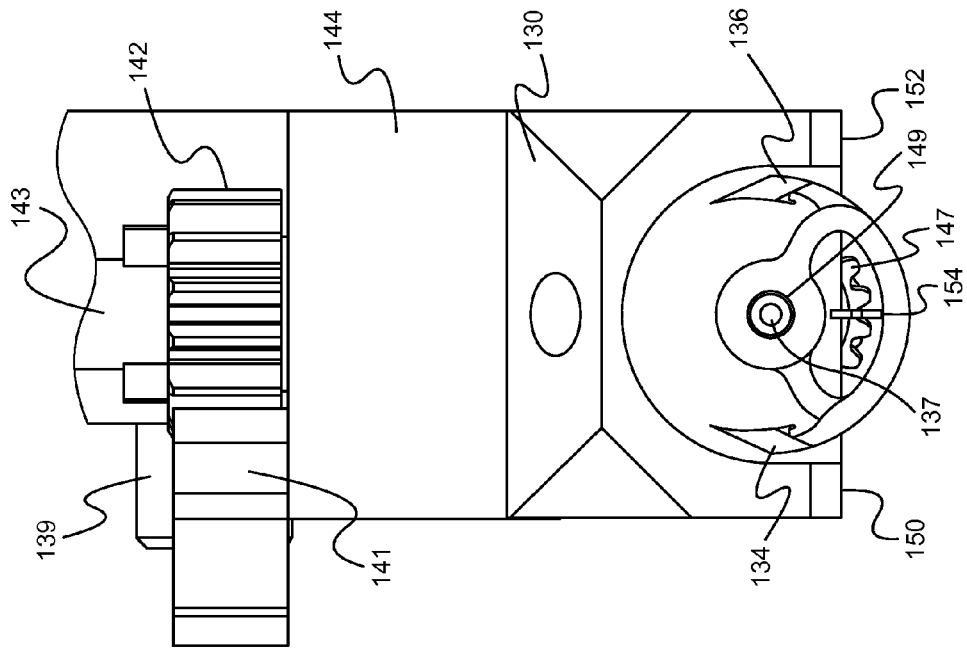
FIG. 23 is an end view of the operating end of FIG. 21 and depicting the insertion needles in a pre-insertion position.
Figure 24:
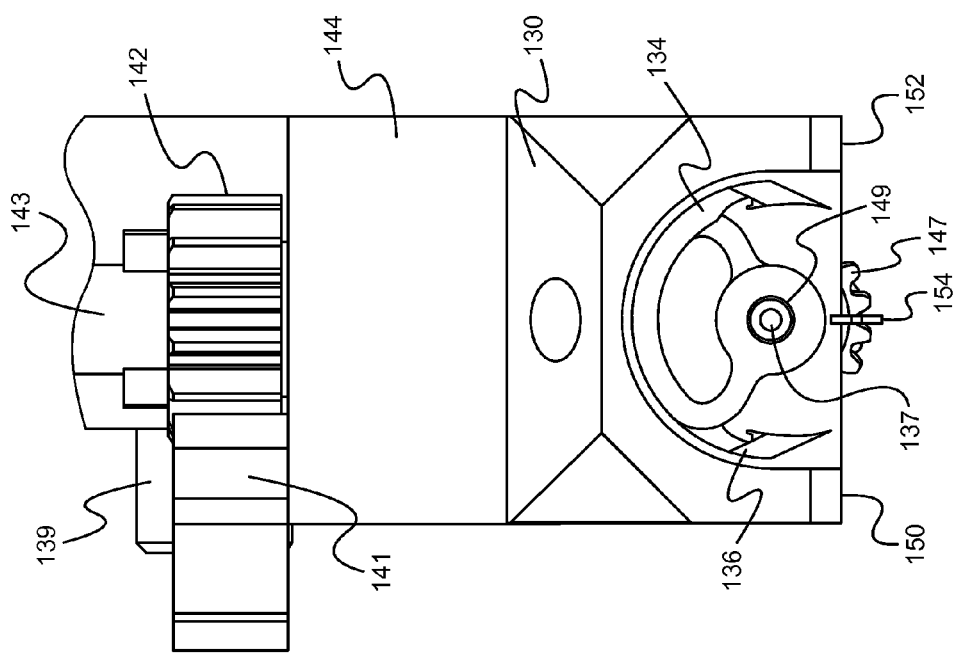
FIG. 24 is an end view similar to FIG. 23 but showing the needles in an engaged position.
Figure 25:
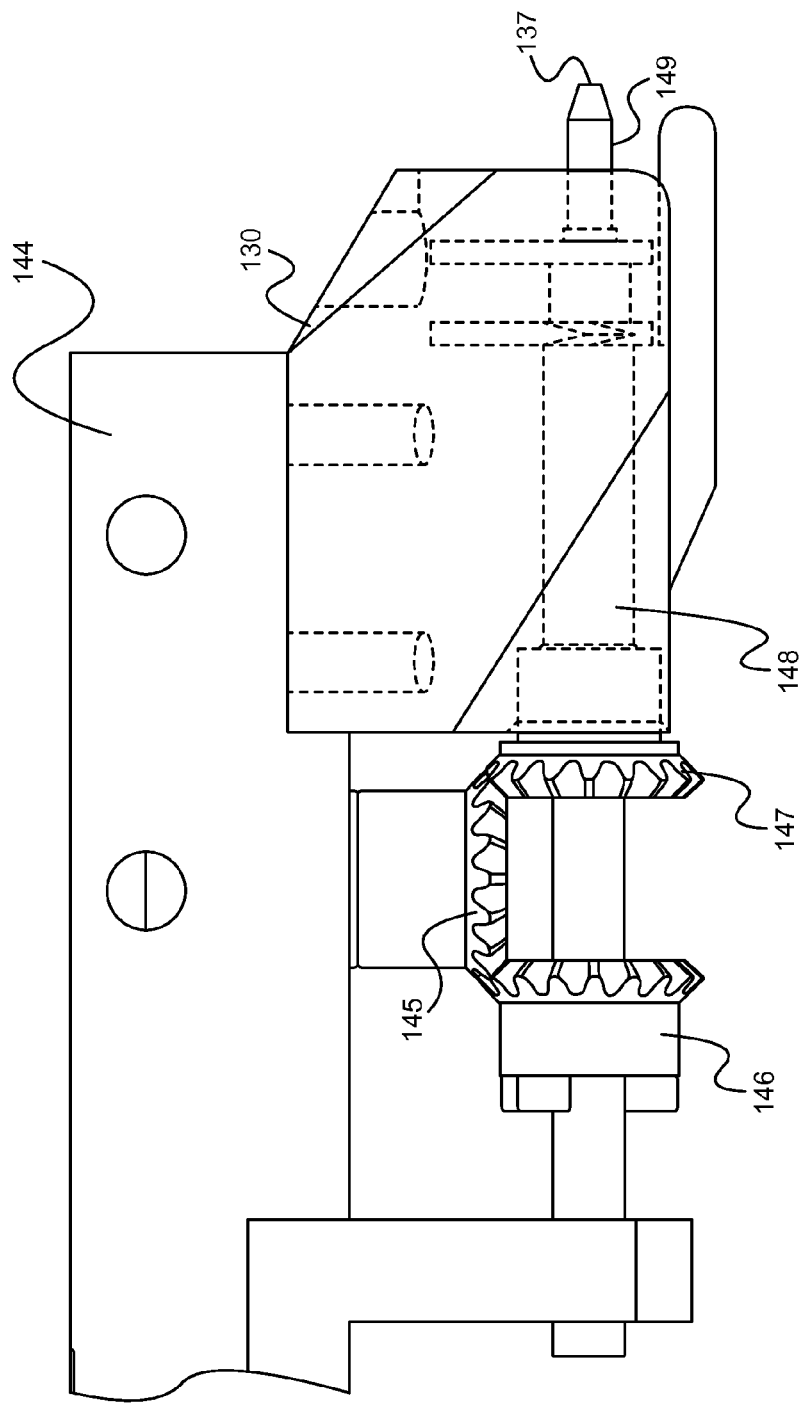
FIG. 25 is a side view of a portion of the drive mechanism and operating end of the suturing tool of FIG. 21.
Figure 26:
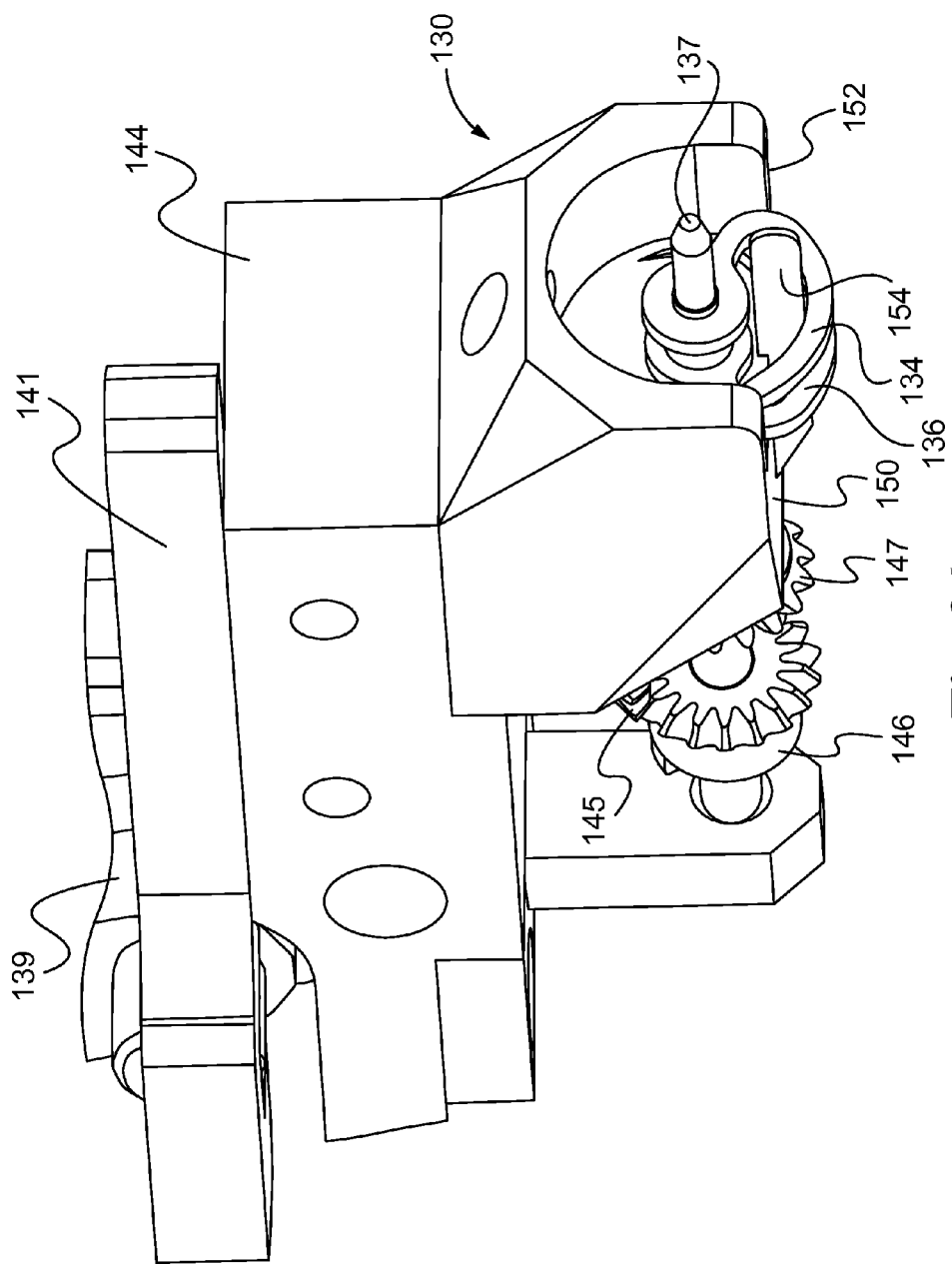
FIG. 26 is a front perspective view of the drive mechanism and operating end of FIG. 25.
Figure 27:
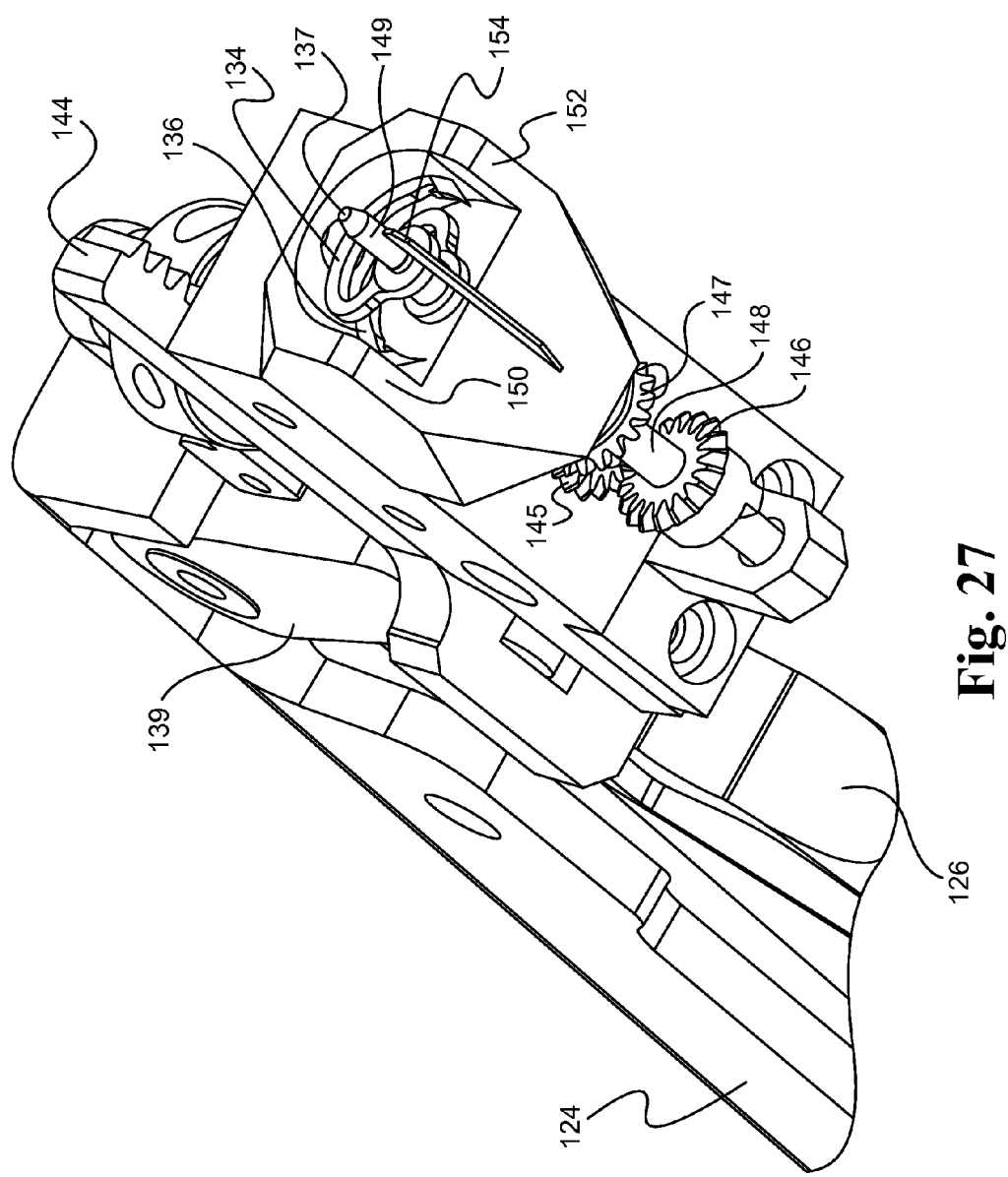
FIG. 27 is a bottom perspective view of the drive mechanism and operating end of FIG. 25.

Starting with FIG. 20A, this shows a closure using manually placed sutures. As shown, the first and second sections of skin 79, 80 are both vertically and horizontally aligned, which would result in a minimum level of scarring. However, as indicated above, such manual insertion is time-consuming, tedious, and exposes healthcare workers to disease transmission through needle-stick injuries. On the contrary, FIG. 20C shows a prior art device which uses automatic insertion of absorbable staples, but as shown, not only are the first and second sections of skin not vertically and horizontally aligned, but result in a substantial ridge 98 extending from the epidermal layer 88 which would form a significant scar on the patient. The resulting closure afforded by the teachings of the present disclosure, on the other hand, is depicted in FIG. 20B. As shown therein, the interface 96 is horizontally and vertically aligned and tightly grouped. In addition, a minimum of scarring will result given this close vertical and horizontal approximation, thus avoiding the unsightly scarring of the prior art device of FIG. 20C. Moreover, as the suturing is performed semi-automatically by the suturing device 20 of the present disclosure, the substantial time commitment required by manual placement of sutures of FIG. 20A is avoided.

Accordingly, a retrograde application of a suture 32 can result in either a closed helix or an open helix configuration depending on the manner in which the suture 32 is set in the starting position and prior to deployment. Although only retrograde applications of both closed and open helix sutures are depicted, it can be seen that an antegrade application of a suture 32 can similarly be used to provide either a closed helix or an open helix suture depending on the manner in which the suture 32 is set in the starting position and prior to deployment.

Referring now to FIGS. 21-27, an alternative embodiment of a suturing tool that can be used against the epidermal layer of the skin is disclosed. In other words, rather than be inserted into an incision such that the needles drive upwardly into the sub-dermal and dermal layers of the skin as with the first embodiment, the alternative embodiment of FIGS. 21-27 is adapted to rest against the outside or epidermal layer of the skin and install sutures downwardly into the epidermal and dermal layers of the skin. As all other features of the alternative embodiment are similar, rather than walk through each element herein, the reader will note the like elements use like reference numerals as with the first embodiment but for the inclusion of a "100" series prefix.

Figure 28:
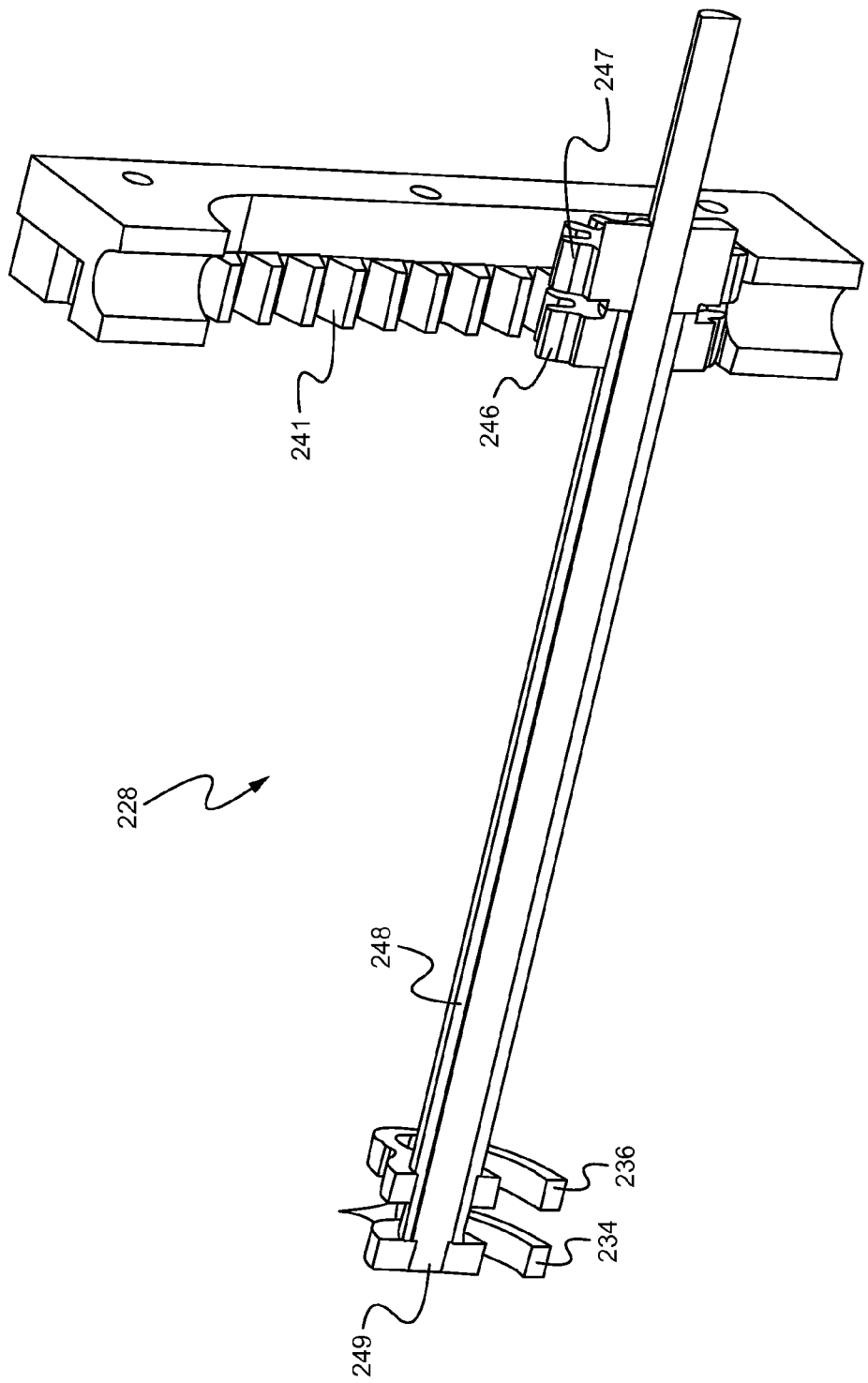
FIG. 28 is a longitudinal cross-sectional view of a test version of a drive mechanism and drive shafts showing the coaxial disposition of the drive shafts for the first and second needles.

Turning to FIG. 28, an alternative embodiment of a drive mechanism 228 for a suturing tool is disclosed. For example, the drive mechanism 228 shown may be used with the test fixture 86 of FIGS. 13-14 so as to provide yet another way to rotate the needles 234, 236 in opposite directions. More specifically, the drive mechanism 228 may include coaxial drive shafts 248, 249, where each coaxial drive shaft 248, 249 is coupled to a corresponding needle 236, 234. Each coaxial drive shaft 248, 249 is further coupled to a corresponding gear 246, 247 such that a rotation of the gears 246, 247 also causes a corresponding rotation of the needles 236, 234. Moreover, the first gear 246 may be driven by the first gear rack 241, while the second gear 247 may be independently driven by a second gear rack 242, which although not shown in FIG. 28 for illustrative purposes, may substantially mirror the first gear rack 241. In the configuration shown, when the gear racks 241, 242 are pushed in a downward direction, the gears 246, 247 are caused to rotate in opposing directions. As the gears 246, 247 rotate, the coaxial drive shafts 248, 249, and thus, the corresponding needles 236, 234 are also caused to rotate in opposing directions so as to install sutures 32 in accordance with the teachings of the present disclosure.

Figure 29:
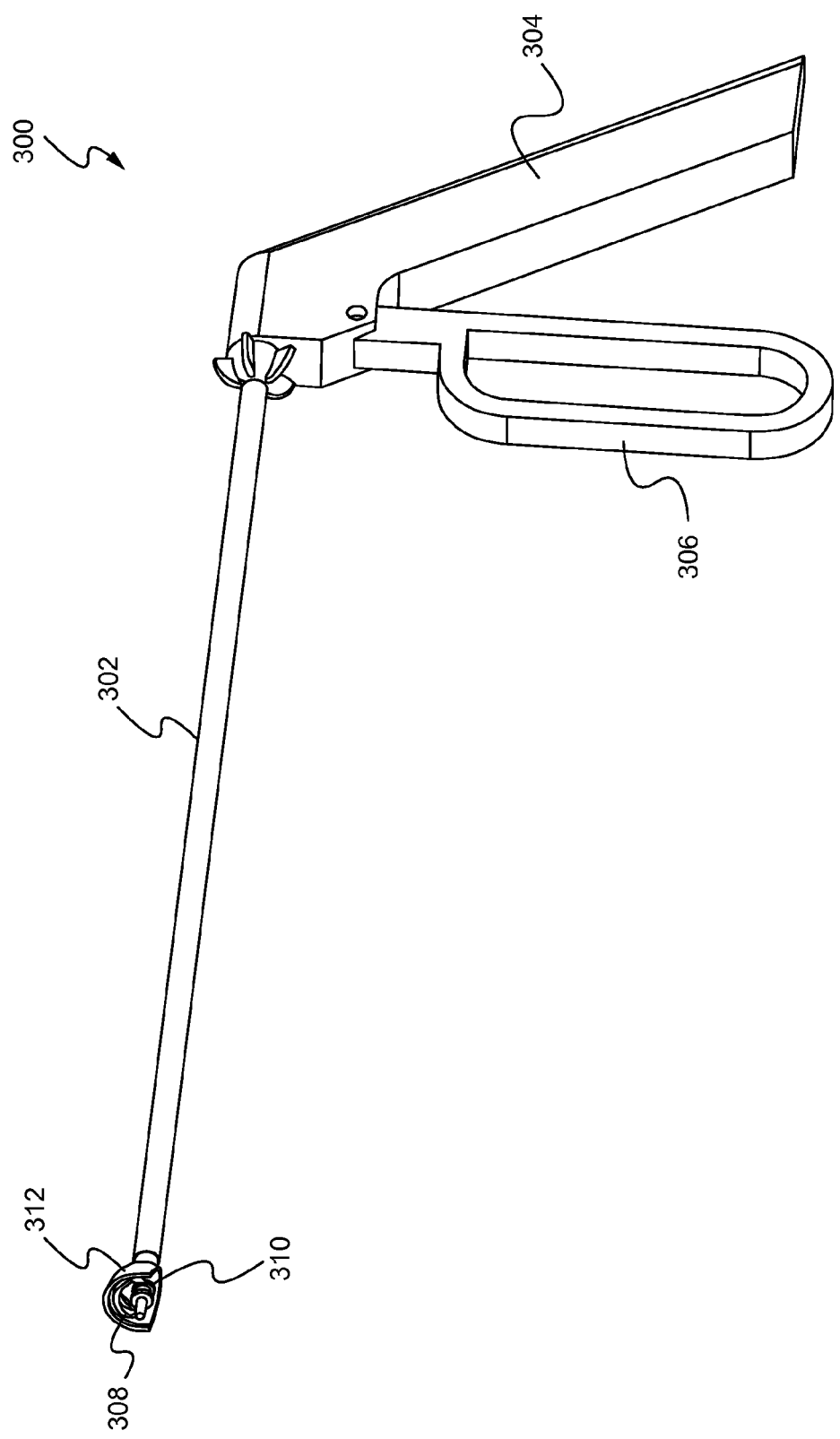
FIG. 29 is a perspective view of a laparoscopic embodiment of a suturing tool constructed in accordance with the disclosure.
Figure 30:
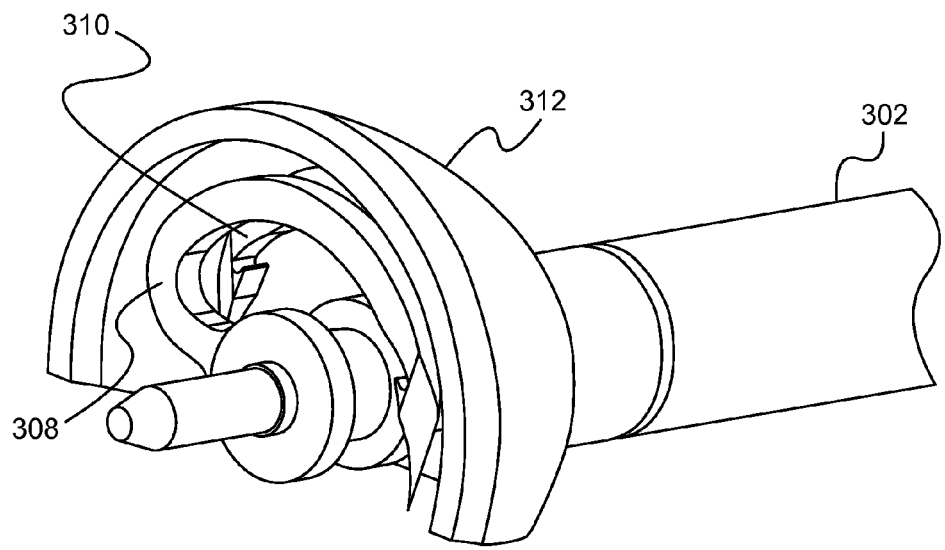
FIG. 30 is an enlarged perspective view of the operating end of the laparoscopic embodiment of FIG. 29, with the needles shown in retracted positions.
Figure 31:
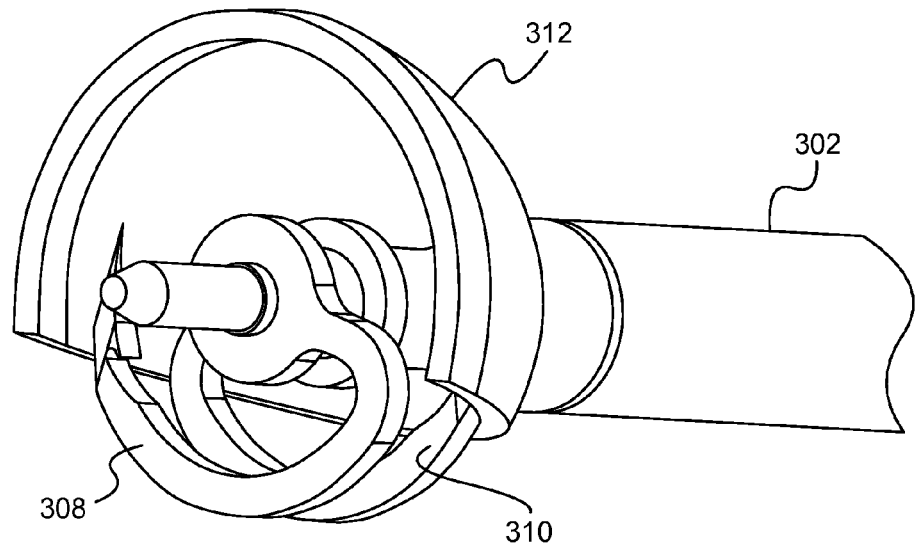
FIG. 31 is an enlarged perspective view of the operating end of the laparoscopic embodiment with the needles shown in extended positions.

The illustration of FIGS. 29-31 depicts still a further embodiment of the present disclosure. In such an embodiment, the suturing tool 300 can be used laparoscopically. In other words, rather than being used on the dermal layer of the skin or even epidermal or sub-dermal, the tool 300 enables sutures to be placed deep within the body cavity. This enables relatively small access port incisions to be made in the skin through which the tool 300 can then be inserted to access the organ, muscular structure or other tissue needing to be sutured. To facilitate such usage, it will be noted that the tool 300 includes an elongated drive shaft 302 that extends from a handle 304 and actuating trigger 306. Similar to the other embodiments, actuation of the trigger 306 causes the needles 308 and 310 to rotate. A shroud 312 surrounds the needles 308 and 310. Such a laparoscopic tool 300 would be used in conjunction with a camera or other navigational tool to enable the needles to be moved to the exact location within the body needing the sutures. From the foregoing, it can be seen that in addition to incision closure market, the teachings of the present disclosure are well suited to laparoscopic and minimally invasive applications. For example, the disclosed fastener technology could be used to fasten prosthetic mesh during laparoscopic hernia repairs. The trend toward more minimally invasive operations will continue to present opportunities for the fastening technology disclosed herein.

From the foregoing, it can be seen that the present disclosure sets forth a medical device adapted to rapidly and reliably install sutures to close openings provided within human skin. The device not only greatly reduces the time required for placement of sutures compared to manual suturing, but also results in highly accurate positioning of the first and second sections of skin along both the horizontal and vertical axes to thus avoid substantial scarring after the healing process. Moreover, through the unique combination of elements set forth in the suturing device, the first and second sections of skin are tightly held together during the healing process to both increase the speed in the healing process and minimize any resulting scarring.

What is claimed is:

1. A method of suturing tissue, comprising:
    positioning a suturing device proximate first and second sections of tissue to be sutured together;
    aligning a suture within the suturing device, the suture having a first needle guide at a first suture end and a second needle guide at a second suture end such that the first and second needle guides are positioned along a rotational path of a first arcuate needle and a second arcuate needle of the suturing device;
    driving first and second arcuate needles in opposing directions of rotation through the first and second needle guides of the suture and into the first and second sections of tissue, the first and second arcuate needles separately entering the first and second sections of tissue;
    seating the first and second needle guides of the suture into a corresponding recess formed on each of the first and second arcuate needles; and
    deploying the suture connecting the first and second sections of tissue upon movement of the first and second arcuate needles.

2. The method of claim 1, wherein the driving is configured to penetrate through a superficial surface of tissue.

3. The method of claim 1, wherein the deploying is performed upon forward rotation of the first and second arcuate needles in an antegrade configuration causing the first and second needle guides being driven into the tissue based on an inward positioning of the recess formed on each of the first and second arcuate needles to engage the first and second needle guides when the first and second arcuate needles enter the tissue.

4. The method of claim 3, wherein in the antegrade configuration the first and second needle guides push the suture through one of the first and second sections of tissue, across an interface between the first and second sections of tissue, and subsequently into the other one of the first and second sections of tissue.

5. The method of claim 1, wherein the deploying is performed upon reverse rotation of the first and second arcuate needles in a retrograde configuration causing the first and second needle guides being pulled through the tissue based on an outward positioning of the recess formed on each of the first and second arcuate needles to engage the first and second needle guides when the first and second needles exit the tissue.

6. The method of claim 1, wherein the deploying is performed such that the suture is transformed from a first configuration to a helical configuration which includes an at least 360 degree looping of the suture, the suture being within at least one plane in the first configuration.

7. The method of claim 1, wherein the tissue is skin.

8. The method of claim 1, wherein the rotational path of the first and second arcuate needles includes a rotation between 180 and 270 degrees for each of the first and second arcuate needles such that the suture is inserted through the first and second sections of tissue and across an interface there between.

9. The method of claim 1, wherein following deploying the suture, the first and second needles have each passed through the first and second sections of tissue and the suture will be transformed from a first configuration into a helical configuration which includes an at least 360 degree looping of the suture.

* * * * *